(12) United States Patent
Narayanan et al.

(10) Patent No.: US 6,943,191 B1
(45) Date of Patent: Sep. 13, 2005

(54) DISUBSTITUTED LAVENDUSTIN A ANALOGS AND PHARMACEUTICAL COMPOSITION COMPRISING THE ANALOGS

(75) Inventors: Venkatachala L. Narayanan, Gaithersburg, MD (US); Edward A. Sausville, Silver Spring, MD (US); Gurmeet Kaur, Germantown, MD (US); Ravi K. Varma, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/623,000

(22) PCT Filed: Feb. 24, 1999

(86) PCT No.: PCT/US99/04002

§ 371 (c)(1),
(2), (4) Date: Oct. 26, 2000

(87) PCT Pub. No.: WO99/43636

PCT Pub. Date: Sep. 2, 1999

Related U.S. Application Data

(60) Provisional application No. 60/076,330, filed on Feb. 27, 1998.

(51) Int. Cl.[7] .................... A61K 31/24; A61K 31/195; C07C 229/00
(52) U.S. Cl. ................. 514/535; 514/563; 560/46
(58) Field of Search ................ 514/535, 563; 560/46

(56) References Cited

U.S. PATENT DOCUMENTS

| | | |
|---|---|---|
| 4,828,568 A | 5/1989 | Konrad et al. |
| 4,833,164 A | 5/1989 | Batt |
| 4,853,403 A | 8/1989 | Shiraishi et al. |
| 4,971,996 A | 11/1990 | Shiraishi et al. |
| 5,122,537 A | 6/1992 | Buzzetti et al. |
| 5,124,354 A | 6/1992 | Green |
| 5,216,023 A | 6/1993 | Literati et al. |
| 5,326,905 A | 7/1994 | Dow et al. |
| 5,328,914 A | 7/1994 | Hocquaux et al. |
| 5,374,652 A | 12/1994 | Buzzetti et al. |
| 5,409,949 A | 4/1995 | Buzzetti et al. |
| 5,436,235 A | 7/1995 | Buzzetti et al. |
| 5,446,168 A | 8/1995 | Ditrich et al. |
| 5,457,105 A | 10/1995 | Barker |
| 5,457,237 A | 10/1995 | Dow |
| 5,488,057 A | 1/1996 | Buzzetti et al. |
| 5,491,147 A | 2/1996 | Boyd et al. |
| 5,506,211 A | 4/1996 | Barnes et al. |
| 5,514,711 A | 5/1996 | Kitano et al. |
| 5,519,018 A | 5/1996 | Matusch et al. |
| 5,554,519 A | 9/1996 | Weber et al. |
| 5,580,888 A | 12/1996 | Warrellow et al. |

(Continued)

FOREIGN PATENT DOCUMENTS

| | | |
|---|---|---|
| GB | 853482 | * 11/1960 |
| WO | WO 93 23364 | 1/1993 |
| WO | WO 93 23364 A | 11/1993 |
| WO | WO 94 26260 | 1/1994 |
| WO | WO 94 26260 A | 11/1994 |
| WO | WO 95 21613 | 8/1995 |
| WO | WO 96 40115 | 2/1996 |

OTHER PUBLICATIONS

Liu et al., "Synthesis and Biological Activity of 5–'(2, 5–dihydroxybenzyl)amino!salicylic Acid Analogs as Inhibitors of EGF Receptor–Associated Protein Tyrosine Kinase," BioOrg. Med. Chem. Lett. (1997), 7(3), 365–368.

Chen et al., "Structure–Activity Relationships in a Series of 5–'(2,5–dihydroxybenzyl)amino!salicylate Inhibitors of EGF–Receptor–Associated Tyrosine Kinase: Importance of Additional Hydrophobic Aromatic Interactions," J. Med. Chem. (1994), 37(6), 845–59.

Chen et al., "Synthesis and Structure–Activity Studies of a Series of '(hydrozybenzyl)amino!salicylates as Inhibitors of EGF Receptor–Associated Tyrosine Kinase Activity," J. Med. Chem. (1993), 36(25), 4094–8.

(Continued)

Primary Examiner—Paul A. Zucker
(74) Attorney, Agent, or Firm—Klarquist Sparkman, LLP

(57) ABSTRACT

Disubstituted lavendustin A analogs that are PTK inhibitors having antiproliferative activity are described. Preferred compounds of the disclosure, without limitation, satisfy either Formula 1 or Formula 2.

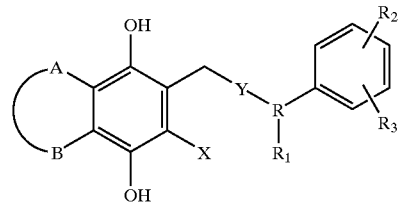

Formula 1

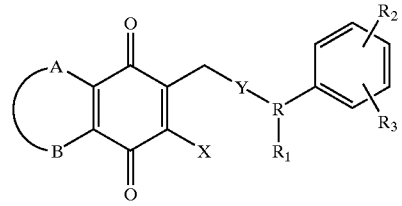

Formula 2

The present disclosure also provides pharmaceutical compositions comprising effective amounts of disubstituted lavendustin A analogs and potentially comprising other active ingredients, other materials conventionally used in the formulation of pharmaceutical compositions, and mixtures thereof. The compounds and compositions of the disclosure can be used for treating subjects to, for example, inhibit the proliferation of living cells in the treatment of proliferative diseases.

22 Claims, No Drawings

U.S. PATENT DOCUMENTS

| | | | |
|---|---|---|---|
| 5,587,385 A | 12/1996 | Buzzetti et al. | |
| 5,587,459 A | 12/1996 | Uckun | |
| 5,593,997 A | 1/1997 | Dow et al. | |
| 5,608,070 A | 3/1997 | Alexander et al. | |
| 5,610,185 A | 3/1997 | Stanwell et al. | |
| 5,616,582 A | 4/1997 | Barker | |
| 5,618,829 A | 4/1997 | Takayanagi et al. | |
| 5,622,977 A | 4/1997 | Warrellow et al. | |
| 5,627,207 A | 5/1997 | Buzzetti et al. | |
| 5,633,257 A | 5/1997 | Warrellow et al. | |
| 5,639,757 A | 6/1997 | Dow et al. | |
| 5,648,378 A | 7/1997 | Huang | |
| 5,650,415 A | 7/1997 | Tang et al. | |
| 5,652,250 A | 7/1997 | Buzzetti et al. | |
| 5,656,654 A | 8/1997 | Buzzetti et al. | |
| 5,661,126 A | 8/1997 | Donahoe et al. | |
| 5,663,346 A | 9/1997 | Buzzetti et al. | |
| 5,674,880 A | 10/1997 | Boyd et al. | |
| 5,677,320 A | 10/1997 | Chandraratna | |
| 5,677,323 A | 10/1997 | Chandraratna | |

OTHER PUBLICATIONS

Chen et al., "Synthesis and Biological Evaluation of Series of Hydroxybenzylphenylamine Derivatives as Inhibitors of EGF Receptor–Associated Tyrosine Kinase Activity," Anti–Cancer Drug Des. (1996), 11(1), 49–71.

Nussbaumer et al., "Novel Antiproliferative Agents Derived from Lavendustin A," J. Med. Chem. (1994), 37(24), 4979–84.

Smyth et al., "Non–Amine Based Analogues of Lavendustin A as Protein–Tyrosine Kinase Inhibitors," J. Med. Chem., 36, 3010–14 (1993).

Gazit et.al., "Tyrophostins. 2. Heterocyclic and $_{60}$–Substituted Benzylidenemalononitrile Tyrphostins as Potent Inhibitors of EGF Receptor and Erb2/neu Tyrosine Kinases," J. Med. Chem., 34, 1896–1907 (1991).

Traxler et al., "Sulfonylbenzoyl–Nitrostyrenes: Potential Bisubstrate Type Inhibitors of the EGF–Receptor Tyrosine Protein Kinase," J. Med. Chem., 34, 2328–37 (1991).

Kaur and Sausville, "Altered Physical States of p210$^{bcr-abl}$ in Tyrphostin AG957–Treated K562 Cells," Anti–Cancer Drugs, 7, 815–24 (1996).

Smyth et al., "Hydroxylated 2–(5'–Salicyl)naphthalenes as Protein–Tyrosine Kinase Inhibitors," J. Med. Chem., 36, 3015–20 (1993).

Burke, Jr., "Protein–Tyrosine Kinases: Potential Targets for Anticancer Drug Development," Stem Cells, 12, 1–6 (1994).

Gazit et al., "Tyrphostins I: Synthesis and Biological Activity of Protein Tyrosine Kinase Inhibitors," J. Med. Chem., 32, 2344–52 (1989).

Liu et al., "Synthesis and Biological Activity of 5–'(2, 5–dihydroxybenzyl)aminosalicylic Acid Analogs as Inhibitors of EGF Receptor–Associated Protein Tyrosine Kinase," BioOrg. Med. Chem. Lett., 7(3), 365–68 (1997).

Chen et al., "Structure–Activity Relationships in a Series of 5–'(2,5–dihydroxybenzyl)aminosalicylate Inhibitors of EGF–Receptor–Associated Tyrosine Kinase: Importance of Additional Hydrophobic Aromatic Interactions," J. Med. Chem., 37, 845–59 (1994).

Chen et al., "Synthesis and Structure–Activity Studies of a Series of [(Hydroxybenzyl)amino]salicylates as Inhibitors of EGF Receptor–Associated Tyrosine Kinase Activity," J. Med. Chem., 36, 4094–8 (1993).

Chen et al., "Synthesis and Biological Evaluation of Series of Hydroxybenzylphenylamine Derivatives as Inhibitors of EGF Receptor–Associated Tyrosine Kinase Activity," Anti–Cancer Drug Des., 11, 49–71 (1996).

Nussbaumer et al., "Novel Antiproliferative Agents Derived from Lavendustin A," J. Med. Chem., 37, 4979–84 (1994).

* cited by examiner

DISUBSTITUTED LAVENDUSTIN A ANALOGS AND PHARMACEUTICAL COMPOSITION COMPRISING THE ANALOGS

This application is a 371 of PCT/US99/04002, filed Feb. 24, 1999, which claims benefit of 60/076,330 filed Feb. 27, 1998.

FIELD OF THE INVENTION

The present invention concerns protein kinase inhibitors, particularly disubstituted analogs of lavendustin A, pharmaceutical compositions comprising these inhibitors, and methods for treating subjects using the analogs and compositions.

BACKGROUND OF THE INVENTION

The growth of cells is believed to be maintained in balance (cytostasis) through the opposing actions of the protein products of promotor and suppressor genes (oncogenes). Mutations of the promotor or suppressor genes result in the production of mutated protein products which are incapable of carrying out their normal growth-enhancing or growth-reducing functions. These proteins are not active themselves. Instead, the proteins are activated by (1) phosphorylation with a nucleoside triphosphate, such as ATP or GTP, and one of several kinases, such as protein tyrosine kinase, or (2) autophosphorylation, i.e., phosphorylations catalytically mediated by the protein itself. These phosphorylations generally occur on the hydroxyl group of tyrosine, serine or threonine residues of the proteins. Phosphorylated protein products of mutated genes are incapable of carrying out their normal functions. Inhibiting the phosphorylation of these mutant proteins should help control cell growth.

Protein tyrosine kinases (PTKs) mediate important signaling events associated with cellular activation, differentiation and mitogenesis. See, for example, Smyth et al. "Non-Amine Based Analogues of Lavendustin A as Protein-Tyrosine Kinase Inhibitors," *J. Med. Chem.*, 36: 3010–3014, 3010 (1993); and Gazit et al. "Tyrphostins. 2. Heterocyclic and α-Substituted Benzylidenemalononitrile Tyrphostins as Potent Inhibitors of EGF Receptor and Erb2/neu Tyrosine Kinases," *J. Med. Chem.*, 34: 1896–1907, 1896 (1991). The generation of mitogenic signals from abnormally expressed or deregulated protein tyrosine kinases is believed to play an important role in the loss of growth control associated with the neoplastic process. Traxler et. al. "Sulfonylbenzoyl-Nitrostyrenes: Potential Bisubstrate Type Inhibitors of the EGF-Receptor Tyrosine Protein Kinase," *J. Med. Chem.*, 34: 2328–2337, 2328 (1991).

PTK inhibitors are useful as antiproliferative therapeutics, as well as pharmacological probes of the biochemical roles played by tyrosine phosphorylation. *J. Med Chem.*, 36, supra., at p. 3010. PTK inhibitors also may be useful for treating chronic myelogenous leukemia (CML). Patients with CML frequently have a cytogenetic abnormality (the Philadelphia chromosome) resulting from reciprocal translocation between chromosome 9 and chromosome 22. Kaur et al., "Tyrphostin Induced Growth Inhibition: Correlation with Effect on $p210^{bcr-abl}$ Autokinase Activity in K562 Chronic Myelogenous Leukemia," *Anti-Cancer Drugs*, 5: 213–222, 213 (1994). Translocation transfers the c-abl non-receptor protein tyrosine kinase protoncogene from its normal position on chromosome 9 into the bcr gene on chromosome 22. Id. An 8 kb mRNA transcript of the bcr-abl fusion gene is translated into a chimeric bcr-abl fusion protein of 210 kDa ($p210^{bcr-abl}$) that exhibits constitutive protein tyrosine kinase activity. The normal, untranslocated c-abl protoncogene product has considerably lower constitutive protein tyrosine kinase (PTK) activity than $p210^{bcr-abl}$. Id. This raises the possibility that specific PTK inhibitors directed at $p210^{bcr-abl}$ could be useful to patients with CML.

Certain tyrphostins, synthetic tyrosine kinase inhibitors, have an antiproliferative mechanism. AG957, for example, appears to induce the formation of covalent adducts involving $p210^{bcr-abl}$ and its associated signaling molecules. Kaur G. and Sausville E., "Altered Physical States of $p210^{bcr-abl}$ in Tyrphostin AG957-Treated K562 Cells," *Anti-Cancer Drugs*, 7: 815–824, 816 (1996). AG957 also is an effective inhibitor of T-cell, antigen-originated signal transduction and cell growth in Jurkat T-ALL (actula lymphatic leukemia) cells. AG957 apparently affects tyrosine kinase signalling by inhibiting MAP kinase activations and phosphorylation of $p210^{cbl}$ protoncogene. There are at least four classes of tyrphostins: (1) benzenemalonitrile compounds; (2) S-aryl benzenemalonitrile compounds, (3) bisubstrate quinoline compounds; and (4) lavendustin-A-like compounds. Id. Lavendustin A, 5-[(2,5-dihydroxy-benzyl)-(2-hydroxy-benzyl)-amino]-2-hydroxy-benzoic acid, is shown below as compound 1.

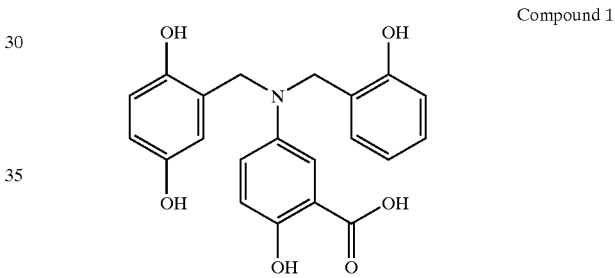

Compound 1

Lavendustin A, a trisubstituted amine, is a natural product inhibitor of the epidermal growth factor receptor (EGFR) PTK, a potent protein tyrosine kinase inhibitor first isolated from *Streptomyces griseolavendus*. Devraj et al.'s "A Versatile Solid Phase Synthesis of Lavendustin A and Certain Biologically Active Analogs," *J. Org. Chem.*, 61: 26 (1996). An active pharmacophore of lavendustin A consists of a more simplified benzylamine, compound 2.

Compound 2

Compound 2 contains the 2,5-dihydroxyphenyl ring of erbstatin, compound 3, as well as the diaryl pattern of piceatannol, compound 4, both of which also are natural product PTK Inhibitors.

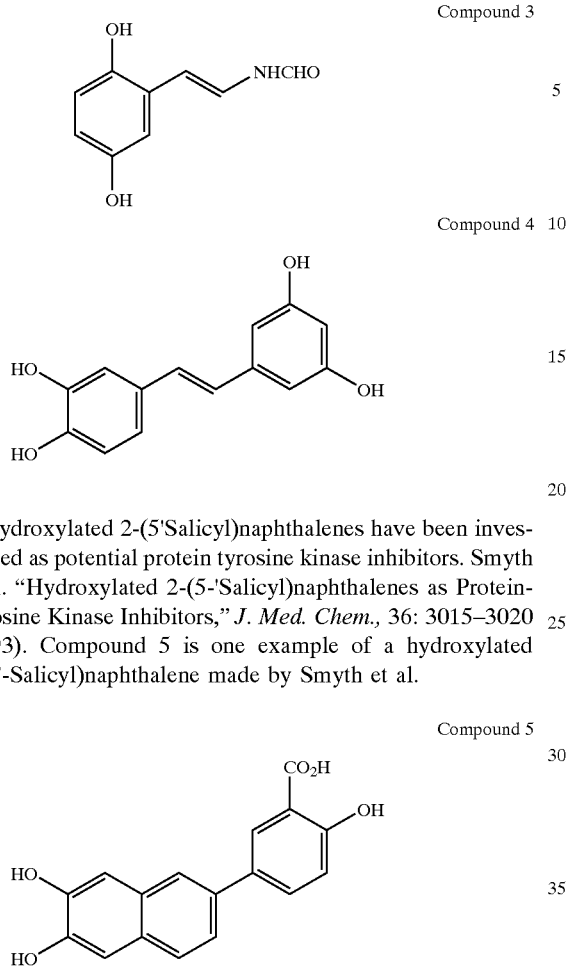

Compound 3

Compound 4

Compound 5

Hydroxylated 2-(5'Salicyl)naphthalenes have been investigated as potential protein tyrosine kinase inhibitors. Smyth et al. "Hydroxylated 2-(5-'Salicyl)naphthalenes as Protein-Tyrosine Kinase Inhibitors," *J. Med. Chem.*, 36: 3015–3020 (1993). Compound 5 is one example of a hydroxylated 2-(5'-Salicyl)naphthalene made by Smyth et al.

But, Smyth et al. concluded that "the resulting salicyl-containing bicyclies exhibited extremely poor inhibitory potency when examined against autophosphorylation of immunoprecipitated p56$^{kL}$ PTK preparations." Id., Abstract, lines 7–9; p. 3017.

The de novo design of PTK inhibitors has been hampered by the lack of three dimensional information regarding PTKs and the interaction of these inhibitors with enzymes. Burke T., "Protein Tyrosine Kinases: Potential Targets for Anti-cancer Drug Development." *Stem Cells*, 12: 1–6, 1 (1994). Burke concluded that significant difficulties were faced b) researchers in this field to develop PTK-inhibitor-based antiproliferatives, primarily because the mechanism of antiproliferative activity is not well understood. Id., at p. 4. This has hampered the development of new PTK-inhibitor-based antiproliferatives. As a result, there still is a need for new PTK-inhibitor-based antiproliferatives useful for treating diseases such as CML.

SUMMARY

The disubstituted lavendustin A analogs of the present invention are PTK inhibitors having antiproliferative activity. Preferred compounds of the present invention, without limitation, satisfy either Formula 1,

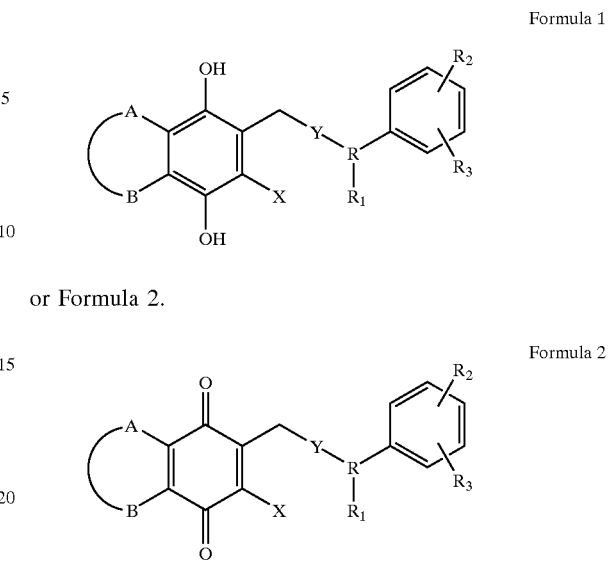

Formula 1 or Formula 2.

Formula 2

With respect to Formula 1, but without limitation, A and B independently are selected from the group consisting of hydrogen and halogen, or are carbon atoms in an aromatic ring; X is either hydrogen or halogen; Y is a single bond or a double bond; R is carbon or nitrogen; $R_1$ is hydrogen or an aliphatic group; $R_2$ is either meta or para to R and is selected from the group consisting of amino, aliphatic amines, aliphatic alcohols, aliphatic amides, aliphatic esters, aliphatic ketones and phosphonic acid esters; and $R_3$ is either ortho, meta or para to R and is selected from the group consisting of hydrogen, hydroxyl and halogen. Preferred compounds satisfying Formula 1 have $R_2$ being para to R and being selected from the group consisting of adamantyl ester, —CH$_2$adamantyl ester, isopropyl ester, methyl ester, t-butyl ester, diisopropyl amide, trifluoromethylisopropyl alcohol, phosphonic acid ester and methyl ketone. Currently preferred compounds, based on in vivo biological activity, are 4'-adamantylbenzoate-1'-N-1,4-dihydroxybenzylamine and 4'-adamantyl methylbenzoate-1'-N-1,4-dihydroxybenzylamine.

With respect to Formula 2, and again without limitation, A and B independently are selected from the group consisting of hydrogen and halogen, or both are carbon atoms in an aromatic ring; X is hydrogen or halogen, Y is either a single bond or a double bond; R is either carbon or nitrogen; $R_1$ is hydrogen or an aliphatic group; $R_2$ is meta or para to R and is selected from the group consisting of amino, aliphatic amines, aliphatic alcohols, aliphatic amides, aliphatic esters, aliphatic ketones and phosphonic acid esters. Good biological results have been observed with those compounds satisfying Formula 2 having $R_2$ para to R and being selected from the group consisting of adamantyl ester, —CH$_2$adamantyl ester, isopropyl ester, and t-butyl ester.

The present invention also provides pharmaceutical compositions comprising an effective amount of a disubstituted lavendustin A analog or an effective amount of a mixture of disubstituted lavendustin A analogs. Such compositions also may comprise other active ingredients, other materials conventionally used in the formulation of pharmaceutical compositions, and mixtures thereof.

The compounds and compositions of the present invention can be used for treating subjects to, for example, inhibit the proliferation of living cells in the treatment of proliferative diseases. A preferred embodiment of the method, without limitation, comprises first providing a compound or compounds, or a composition comprising the compound or compounds, satisfying Formula 1 or Formula 2. An effective amount of the compound, mixture of compounds, or compositions comprising the compound or compounds, is then administered to the subject, preferably orally or intravenously.

DETAILED DESCRIPTION

I. COMPOUNDS

Compounds of the present invention satisfy either Formula 1 or Formula 2 below. Persons of ordinary skill in the an will realize that Formula 2 is the quinone derivative of Formula 1.

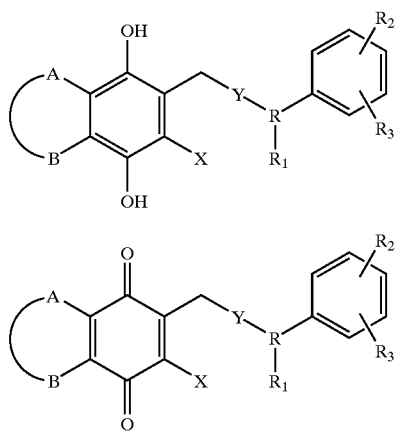

Formula 1

Formula 2

With reference to Formula 1. A and B independently are selected from the group consisting of hydrogen and halogen, or are both carbon atoms in an aromatic ring, preferably a benzene ring, or one or both of A and B is/are oxygen or nitrogen in a heterocycle. A and B preferably are either both hydrogen, or are carbon atoms in a benzene ring. X is a either hydrogen or halogen, such as bromine or chlorine. Y is a single bond or a double bond, and preferably is a single bond. R is either carbon or nitrogen, and preferably is nitrogen. $R_1$ is hydrogen or an aliphatic group, preferably lower alkyl groups. As used herein, "lower" refers to carbon chains having 10 or fewer carbon atoms. "Lower alkyl" refers to carbon chains having ten or fewer carbon atoms, and also includes straight chains, branched chains, and all stereoisomers. $R_2$ typically is at position 3 or 4 relative to R, i.e., meta or para to R, preferably para, and is selected from the group consisting of amino, aliphatic amines, aliphatic alcohols, aliphatic amides, aliphatic esters, aliphatic ketones, carboxyl, and phosphonic acid esters, the aliphatic groups comprising from 1 to about 30 carbon atoms, preferably from about 3 to about 30 carbon atoms, and even more preferably from about 3 to about 16 carbon atoms. $R_2$ preferably is selected from the group consisting of lower alkyl esters, adamantyl esters, adamantylalkyl esters, such as adamantylmethyl esters, adamantylamino, adamantylalkylamino, lower alkyl and haloalkyl alcohols, lower alkyl amides, lower alkyl ketones and phosphonic acid esters. $R_1$ is either ortho, meta or para to R, preferably meta or para, and even more preferably meta, and is selected from the group consisting of hydrogen, hydroxyl and halogen.

Good biological results have been observed with compounds satisfying Formula 1. Certain representative compounds are listed in Table 1, where A and B are independently selected from the group consisting of hydrogen and halogen; X is hydrogen or halogen; Y is a single bond; R is nitrogen; $R_1$ is hydrogen; $R_2$ is selected from the group consisting of adamantyl ester, —$CH_2$adamantyl ester, isopropyl ester, methyl ester, t-butyl ester, diisopropyl amide, trifluoromethylisopropyl alcohol, phosphonic acid ester and methyl ketone; and $R_3$ is selected from the group consisting of hydrogen, hydroxyl and halogen. Particular examples of compounds satisfying Formula 1 include 4'-adamantylbenzoate-1'-N-2,5-dihydroxybenzylamine, 4'-4'-adamantylmethylbenzoate-1'-N-2,5-dihydroxybenzylamine, 5'-chloro-4'-isopropylbenzoate-1'-N-2,5-dihydroxybenzylamine, 4'-(trifluoromethylethanol)-1'-N-2,5-dihydroxybenzylamine, 4'-phenylphosphonate-1-N-2,5-dihydroxybenzylamine, 4'-isopropylbenzoate-1'-N-5-bromo-2,5-dihydroxybenzylamine, 4'-chloro-5'-methylbenzoate-1'-N-3-bromo-2,5-dihydroxybenzylamine, 5'-hydroxy-4'-methylbenzoate-1'-N-5-bromo-2,5-dihydroxybenzylamine, 4'-t-butylbenzoate-1'-N-2,5-dihydroxybenzylamine, 4'-diisopropylbenzamide-N-2,5-dihydroxybenzylamine, and 4'-acetophenone-1'-N-2,5-dihydroxybenzylamine (compound 17).

TABLE 1

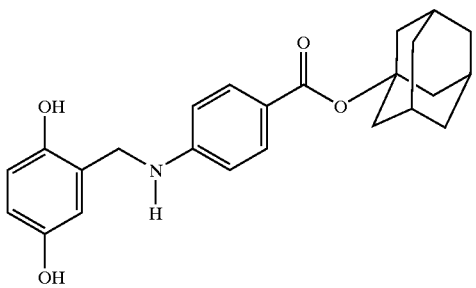

Compound 6

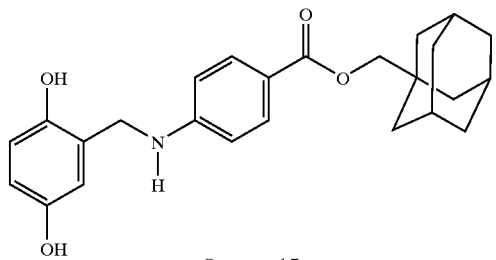

Compound 7

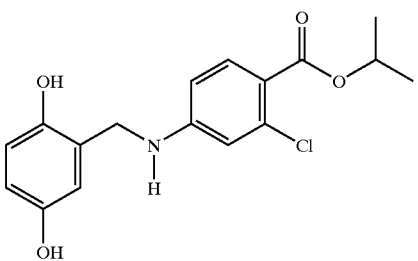

Compound 8

TABLE 1-continued

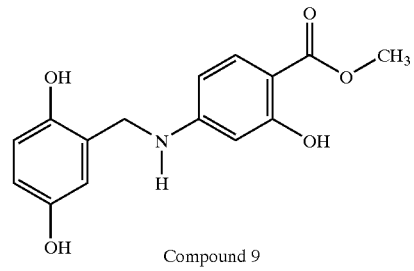
Compound 9

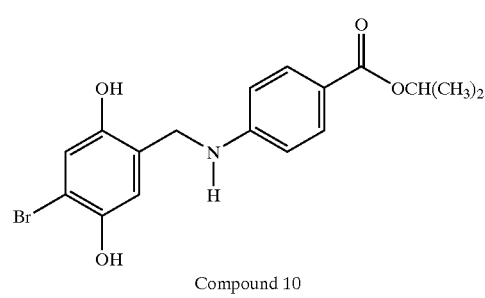
Compound 10

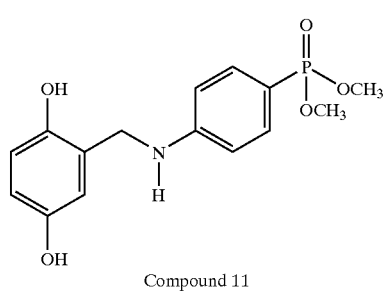
Compound 11

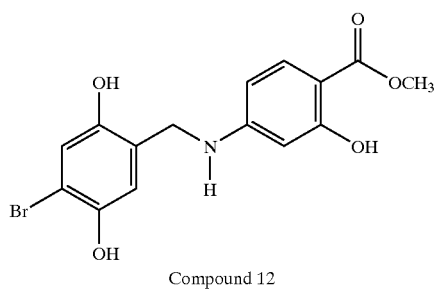
Compound 12

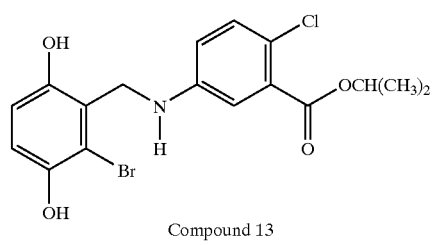
Compound 13

TABLE 1-continued

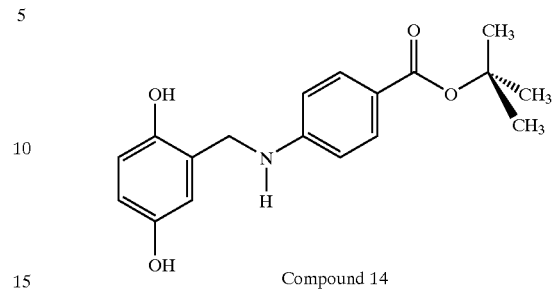
Compound 14

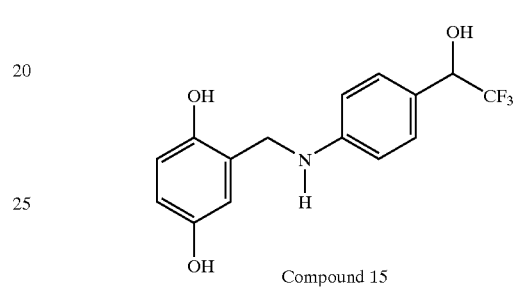
Compound 15

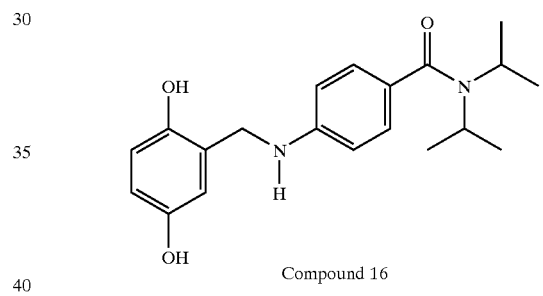
Compound 16

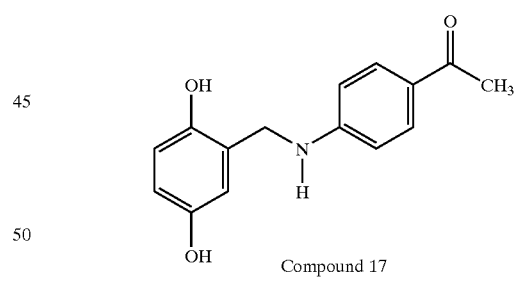
Compound 17

Compounds 18 (1,4-methylbenzoate-1'-N-2,5-dihydroxybenzylamine) and 19 (4'-methylbenzoate-1'-N-1,4-methylnaphthoquinone amine) are examples of compounds satisfying Formula 1 where A and B are carbon atoms in an aromatic ring.

With reference to Formula 2. A and B independently are selected from the group consisting of hydrogen and halogen, or both are carbon atoms in an aromatic ring, or one or both Compound 18

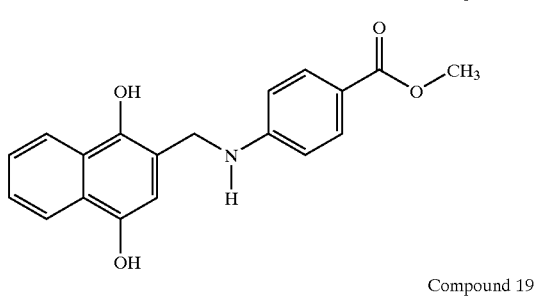

Compound 19

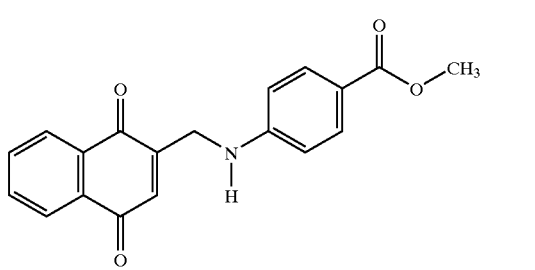

of A or B is/are oxygen or nitrogen in a heterocyclic. X is hydrogen or halogen, such as bromine or chlorine. Y is either a single bond or a double bond, and preferably is a single bond. R is either carbon or nitrogen, and preferably is nitrogen. $R_1$ is hydrogen or a lower aliphatic group, preferably a lower alkyl group. $R_2$ typically is at position 3 or 4 relative to the position of R, i.e., meta or para to R, and preferably is para with respect to R, and is selected from the group consisting of amino, aliphatic amine, aliphatic alcohols, aliphatic amides, aliphatic esters, aliphatic ketones and phosphonic acid esters, with the aliphatic groups preferably comprising from about 1–30 carbon atoms, preferably from about 3 to about 30 carbon atoms, even more preferably from about 3 to about 16 carbon atoms. $R_2$ preferably is selected from the group consisting of adamantyl ester, alkyladamantyl ester, such as —$CH_2$adamantyl ester, isopropyl ester, methyl ester, and t-butyl ester. $R_3$ can be at positions 2, 3 or 4 relative to R, i.e., ortho, meta or para to R, and preferably is meta to R, and is selected from the group consisting of hydrogen, hydroxyl and halogen.

Good biological results have been observed with compounds satisfying Formula 2. Certain representative compounds are listed in Table 2 where A and B are hydrogen; X is hydrogen or halogen; Y is a single bond; R is nitrogen; $R_1$ is hydrogen; $R_2$ is selected from the group consisting of aliphatic esters; and $R_3$ is selected from the group consisting of hydrogen, hydroxyl and halogen. Particular compounds satisfying Formula 2 can be selected, without limitation, from the group consisting of 3'-hydroxy-4'-methylbenzoate-1'-N-p-quinone-2-methyl amine (compound 20), 4'-isopropylbenzoate-1'-N-p-quinone-2-methyl amine (compound 21), 4'-adamantylbenzoate-1'-N-p-quinone-2-methyl amine (compound 22), 4'-adamantylbenzoate-1'-N-2-bromo-p-quinone-3-methyl amine (compound 23), 4'-t-butylbenzoate-1'-N-2-bromo-p-quinone-3-methyl amine (compound 24), 3'-chloro-4'-methylbenzoate-1'-N-2-bromo-p-quinone-3-methyl amine (compound 25) and 3'-chloro-4'-isopropylbenzoate-1'-N-p-quinone-2-methyl amine (compound 26).

TABLE 2

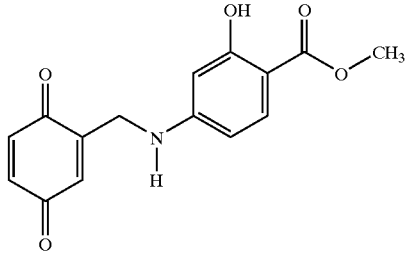

Compound 20

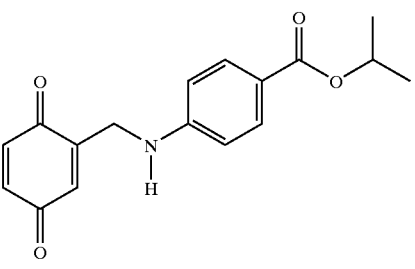

Compound 21

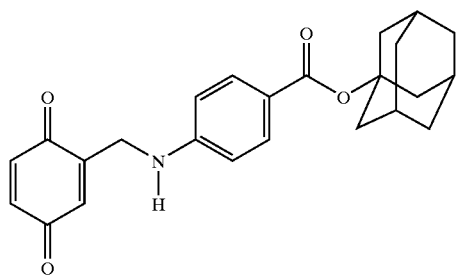

Compound 22

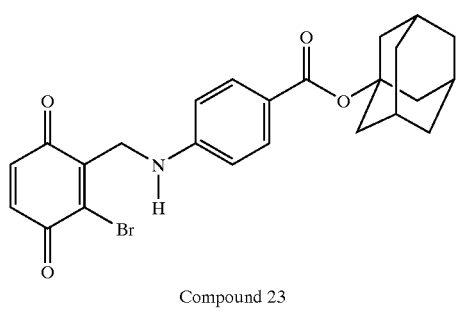

Compound 23

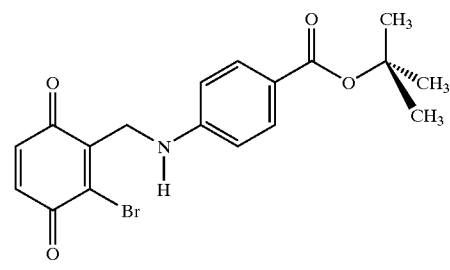

Compound 24

TABLE 2-continued

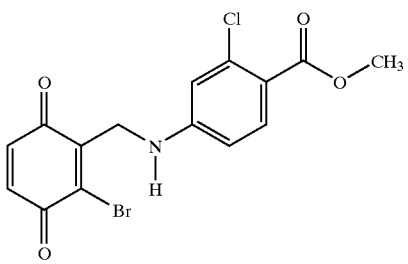

Compound 25

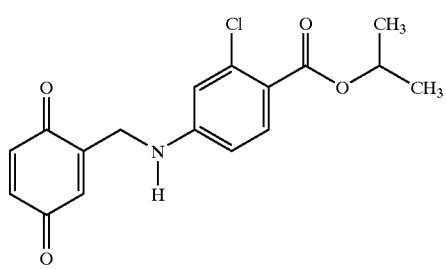

Compound 26

The compounds listed above as satisfying Formulas 1 and 2 have R being a nitrogen atom. Compounds also have been made where R is a carbon atom, and representative compounds are listed in Table 3.

TABLE 3

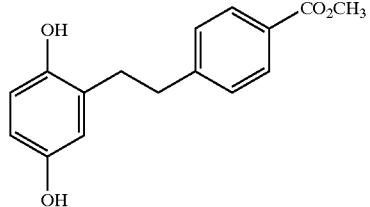

Compound 27

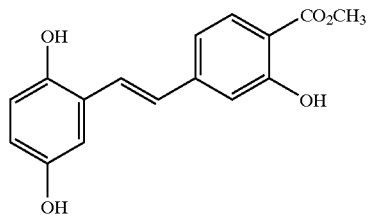

Compound 28

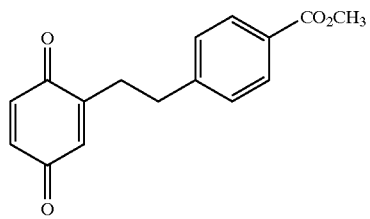

Compound 29

TABLE 3-continued

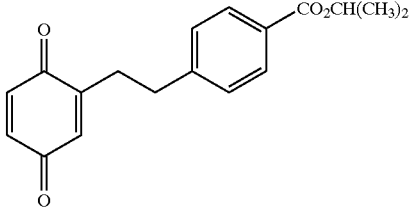

Compound 30

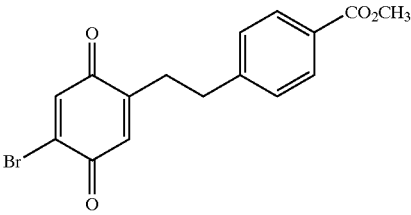

Compound 31

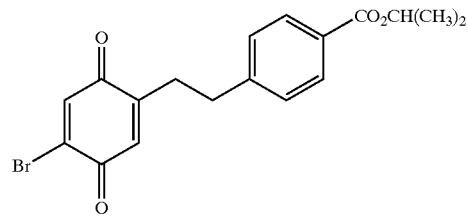

Compound 32

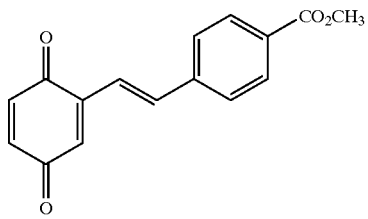

Compound 33

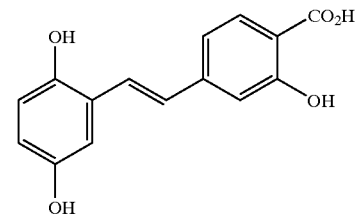

Compound 34

II. SYNTHESIS OF COMPOUNDS

Compounds satisfying Formulas 1 and 2 generally can be synthesized by joining two halves of the molecules through formation of bond Y. For example, with R=N in Formulas 1 and 2, the Y bond can be formed by condensing 2,5-dihydroxybenzaldehyde (compound 27) with a phenylamine (compound 28) having desired substituents, e.g., esters. This has been accomplished by dissolving 2.5-dihydroxybenzaldehyde in ethanol containing $NaHCO_3$, and reacting this with approximately an equimolar amount of a desired phenylamine to form an imine (compound 29). The imine was then catalytically hydrogenated ($H_2$/Pd/C) to form the amine (compound 30). See Scheme 1 and Example 1 below.

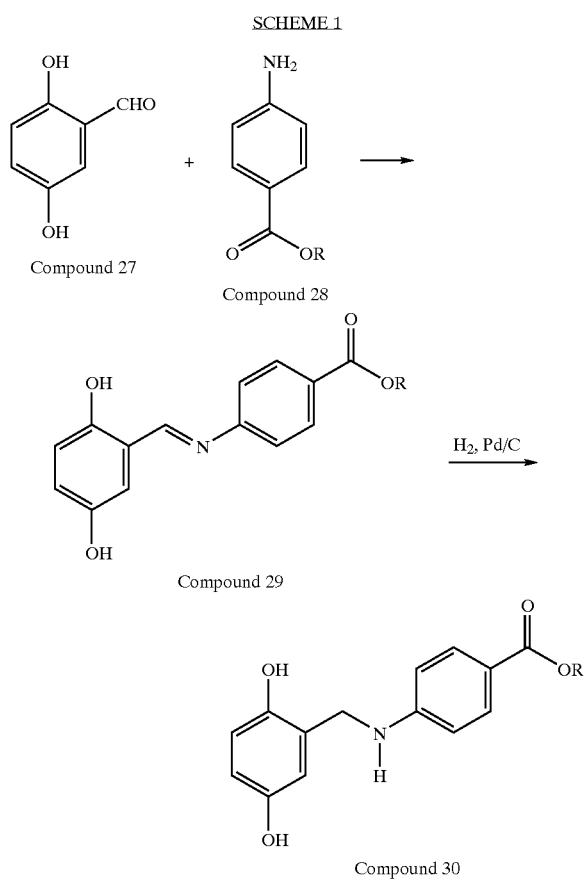

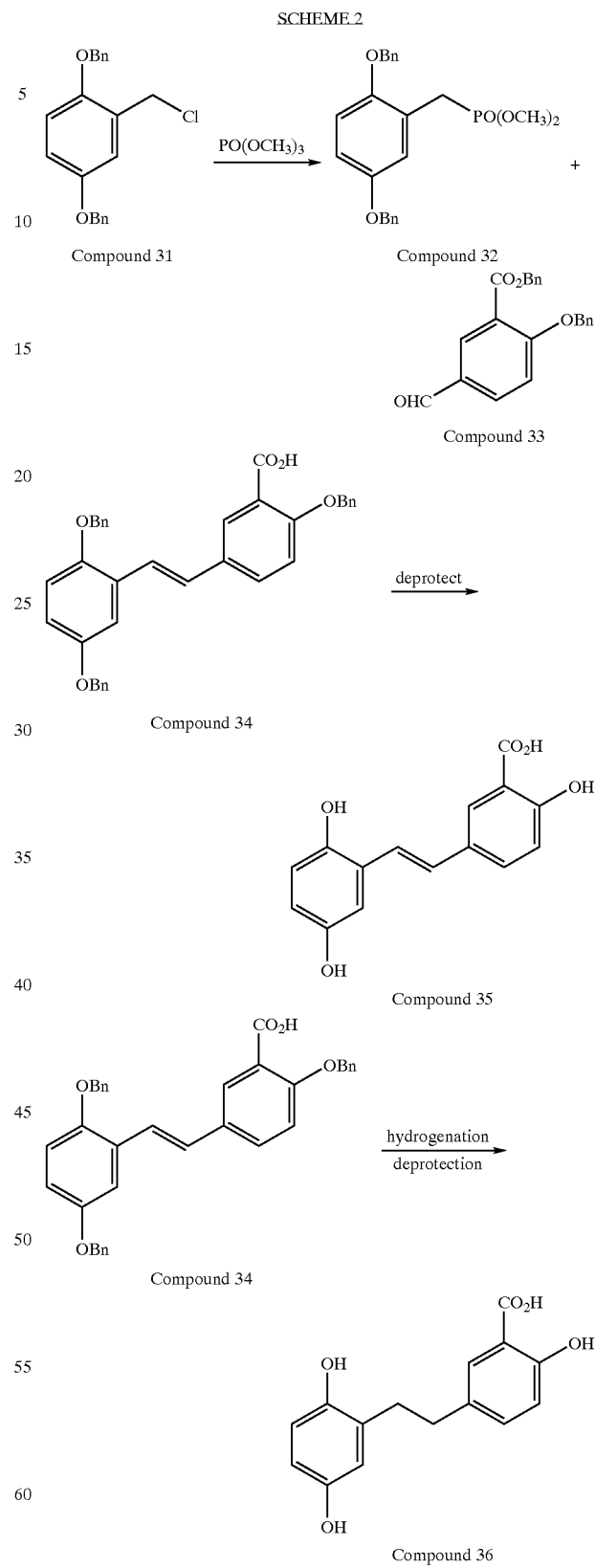

Thus, 4-hydroxyphenols or quinone derivatives can be coupled through formation of the bond Y to aryl amino aliphatic esters, aryl amino aliphatic alcohols, aryl amino aliphatic ketones, aryl amino aliphatic amides, etc. to form compounds satisfying Formulas 1 and 2.

With R=C in Formulas 1 and 2, the Y bond can be formed by Emmons condensation of the appropriate phosphonic acid (formed from the corresponding benzyl halide) with a desired aryl aldehyde derivative. With reference to Scheme 2, a protected dihydroxy benzyl chloride (compound 31) is reacted with a phosphonic acid ester to produce a phosphoric acid (compound 32). The phosphonic acid is coupled via Emmons condensation with an aldehyde (compound 33). The condensation reaction and workup also cleaves the benzoate ester to provide a carboxylic acid (compound 34). The hydroxyl groups of the carboxylic acid are then deprotected to give a carboxylic acid polyol (compound 35). Esterification or amide formation, for example, with the desired group provides compounds according to the present invention where Y is a double bond and R is carbon.

Compounds where Y is a single bond also can be made according to this method. Protected carboxylic acid (compound 34) or the carboxylic acid polyol (compound 35) is hydrogenated to saturate the alkene. Subsequent deprotection results in the formation of the carboxylic acid polyol (compound 36).

Additional details concerning procedures for forming compounds similar to those discussed above are provided by, for example: (1) Gazit A. et al. "Tyrphostins I: Synthesis and Biological Activity of Protein Tyrosine Kinase Inhibitors," *J. Med. Chem.,* 1989, 32: 2344–2352 (1989): and (2) Gazit A. et al., "Tyrphostins. 2. Heterocyclic and α-Substituted Benzylidememalononitrile Tyrphostins as Potent Inhibitors of EGF Receptor and ErbB1/neu Tyrosine Kinases," *J. Med. Chem.* 34: 1897–1907 (1991). These references are incorporated herein by reference.

A solid-phase synthesis of the natural product lavendustin A has been reported. Devraj et al. "A Versatile Solid Phase Synthesis of Lavendustin A and Certain Biologically Active Analogs," *J. Org. Chem.,* 61, No. 26 (1996), which is incorporated herein by reference. This solid-phase synthetic methodology can be adapted for synthesizing compounds satisfying Formulas 1 and 2.

Additional details concerning the synthesis of several representative compounds listed in Tables 1–3 are provided in Examples 2–9.

III. COMPOSITIONS

The compounds described herein can be formulated into compositions for administration to humans and animals to, for example, inhibit the proliferation of living cells. Such compositions include "effective amounts" of the compounds described above, and may further comprise inert carriers, excipients, diagnostics, direct compression binders, buffers, stabilizers, fillers, disintegrants, flavors, colors, lubricants, other active ingredients, other materials conventionally used in the formulation of pharmaceutical compositions, and mixtures thereof.

The method of the present invention comprises administering to humans or animals "effective amounts" of a compound, a mixture of compounds, or compositions comprising "effective amounts" of a compound or mixture of compound. Persons of ordinary skill in the an will realize that an "effective amount" varies. It currently is believed that "administering an effective amount" comprises administering to subjects a total amount of compound per treatment of from about 0.3 cram to about 3 grams, preferably from about 0.5 gram to about 1 gram, of a compound or compounds, or compositions comprising the compound(s), according to the present invention. In vivo tests with mice have indicated that a dose of from about 30 mg/kg/dose to about 50 mg/kg/dose also provides an "effective amount." Moreover, it typically is desirable to provide as large a dose as possible to a subject, depending upon the ability of the subject receiving the compound, or compositions comprising the compound (s), to tolerate the dose.

Tests performed using nearly sixty different cancer cell lines (see Examples below) indicate that the cytotoxic profile of the compounds of the present invention share certain similarities with other agents that are useful as antineoplastics. Thus, it would be within the purview of persons skilled in the art of preparing pharmaceutical formulations to add such compounds to pharmaceutical inert carriers, excipients, etc. suitable for administration to a subject, in a manner similar to that used for preparing such formulations of known antineoplastics. Compounds of the present invention can be administered to subjects using dosage protocols that are substantially similar to protocols used with other antineoplastics.

The compounds or compositions can be administered by any number of methods including, but not limited to, topically, orally, intramuscularly, intranasally, subcutaneously, intraperitoneally, intralesionally or intravenously. Currently, oral and intravenous administration are believed to be the preferred methods for administering compounds and compositions of the present invention.

IV. BIOLOGICAL RESULTS

Compounds satisfying Formulas 1 and 2 have been made and subjected to various tests to evaluate biological activity For example, cell culture and cell growth assays and inhibition of in vivo auto-phosphorylation of $p210^{bcr-abl}$ in immune-complex kinase assays have been conducted. Experimental procedures for these biological assays are provided below in Examples 10–11. Results of these assays for representative compounds satisfying formulas 1 and 2 are provided below in Table 4. An $IC_{50}$ of 50 micromolar or less is considered effective.

TABLE 4

| Compound | $IC_{50}$ (6d MTT) μM | $IC_{50}$ ($p210^{bcr-abl}$ in vitro phosphorylation) μM |
| --- | --- | --- |
| 13 | 18 | 10 |
| 14 | 7 | 10 |
| 30 | 26 | 25 |
| 31 | N/A | N/A |
| 32 | 10 | No Effect |
| 33 | 7.5 | No Effect |

Compounds of the present invention also have been subjected to the drug screening procedure employed by the National Cancer Institute for the screening of drugs having possible anticancer utility. The screening procedure uses a diverse, disease-oriented panel consisting of approximately 60 different human tumor cell lines organized into disease-specific subpanels. The compounds of the present invention were tested over a range of concentrations for cytotoxic or growth-inhibitory effects against cell lines comprising the panel. The eight subpanels represented diverse histologies (leukemias, melanomas, and tumors of the lung, colon, kidney, breast, ovary, and brain).

Compounds of the present invention were tested over a period of two days. During this period the cells were continuously exposed to various concentrations of the compounds tested. The tests produced individual dose-responses, one for each cell line (i.e. one for each example), and the data were represented in dose-response curves. The data provided by these dose response curves were summarized using a mean-graph format.

To produce data for the mean-graph format, a compound concentration that produced a target level response was calculated for each cell line. Three different response parameters were evaluated. The first response parameter was the growth inhibition ("$GI_{50}$"). $GI_{50}$ is the concentration of compounds made according to the present invention that produced an apparent 50% decrease in the number of tumor cells relative to the appropriate control (not exposed to the compounds of the present invention) at the end of the incubation period.

The second response parameter was the total growth inhibition ("TGI"). TGI is the concentration at which the number of tumor cells remaining at the end of the incubation period substantially equal the number of tumor cells existing at the start of the incubation period.

The third response parameter was the lethal concentration ("$LC_{50}$") $LC_{50}$ is the concentration of compounds made according to the present invention that caused an apparent 50 percent reduction in the number of tumor cells relative to the appropriate control (not exposed to the compounds of the present invention) at the start of the incubation period.

In a typical $GI_{50}$ mean graph, the relative position of the vertical reference line along the horizontal concentration axis was obtained by averaging the negative $\log_{10}GI_{50}$ values for all the cell lines tested against the compound. Horizontal bars were then plotted for the individual negative $\log_{10}GI_{50}$ values of each cell line relative to the vertical reference line. The $GI_{50}$ graph thus provided a characteristic fingerprint for the compound, displaying the individual cell lines that are proportionately more sensitive than average (bars extending to the right of the reference line) or proportionately less sensitive than average (bars extending to the left of the reference line). The length of a bar was proportional to the difference between the $\log_{10}GI_{50}$ value obtained with the particular cell line and the mean (represented by the vertical reference line).

Similar mean graphs were prepared for the TGI and $LC_{50}$ response parameters.

Cancer cell line data was compared to data for the known compound AG-957 and for seven compounds of the present invention. The results showed that the compounds of the present invention have antiproliferative effects against many of the cancer cell lines tested.

Compounds satisfying Formulas 1 and 2 also have been tested for in vivo activity in the hollow fiber assay. See Example 12 below for the procedure used for the in vivo tests. Each compound tested was tested against a minimum of 12 human cancer cell lines. Data is reported as % T/C (i.e., the percentage of mice surviving less than control mice) for each of the 2 compound doses against each of the cell lines with separate values calculated for the intraperitoneal and subcutaneous samples, with a target value for % T/C being about 50 or less.

Compounds were selected for further in vivo testing in standard subcutaneous xenograft models on the basis of several hollow fiber assay criteria. These criteria include: (1) a % T/C of 50 or less in 10 of the 48 possible test combinations (12 cell lines×2 sites×2 compound doses); (2) activity at a distance (intrapentoneal drug/subcutaneous culture) in a minimum of 4 of the 24 possible combinations; and/or (3) a net cell kill of 1 or more cell lines in either implant site. To simplify evaluation, a point system has been adopted which allows rapid assessment of a compound's activity. A value of 2 is assigned for each compound dose which results in a 50% or greater reduction in viable cell mass. The intraperitoneal and subcutaneous samples were scored separately so that criteria (1) and (2) could be evaluated. Compounds with a combined IP+SC score≧20, an SC score≧8, or a net cell kill of one or more cell lines were referred for xenograft testing. These criteria have been statistically validated by comparing the activity outcomes of greater than 80 randomly selected compounds in the hollow fiber assay and in the xenograft testing.

By applying these criteria the compounds of the present invention have proved promising as anticancer agents. Especially promising are the following adamantyl ester derivatives, Compounds 6 and 7.

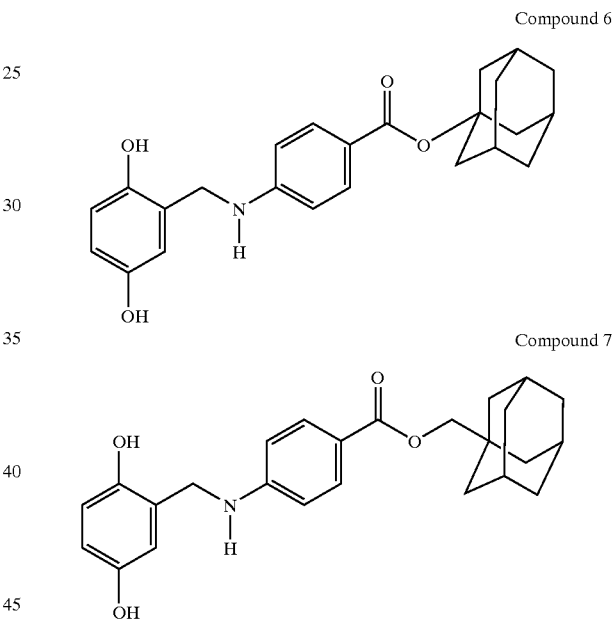

Compound 6

Compound 7

Presented below in Tables 5–7 are the in vivo test results for Compound 6, which has an IP+SC score of 16 and an SC score of 8.

TABLE 5

| Grp No. | Compound No. | Dose/Units | Rt | Schedule | No. of Mice | No. of Fibers | NCI-H23 IP | NCI-H23 SC | MDA-MB-231 IP | MDA-MB-231 SC | SW-620 IP | SW-620 SC |
|---|---|---|---|---|---|---|---|---|---|---|---|---|
| 3 | 6 | 50.00 mg/kg/dose | IP | QD X 4, Day 4 | 3 | 3 | >100 | >100 | >100 | 92 | >100 | 80 |
| 4 | 6 | 33.50 mg/kg/dose | IP | QD X 4, Day 4 | 3 | 3 | 100 | >100 | >100 | 67 | >100 | 94 |

VEHICLES
Grp 3 –> Compound No. 6 1 (Dose = 50.00): in Saline + Tween 80 (0.05%) (Unknown) Inj. Vol.: 0.1 ml/10 gm body wt
Grp 4 –> Compound No. 6 1 (Dose = 33.50): in Saline + Tween 80 (0.05%) (Unknown) Inj. Vol.: 0.1 ml/10 gm body wt

TABLE 6

| | TREATMENT | | | | | | % T/C | | | | | |
|---|---|---|---|---|---|---|---|---|---|---|---|---|
| | Compound | | | | No. of | No. of | OVCAR-5 | | MDA-MB-435 | | SF-295 | |
| Grp No. | No. | Dose/Units | Rt | Schedule | Mice | Fibers | IP | SC | IP | SC | IP | SC |
| 3 | 6 | 50.00 mg/kg/dose | IP | QD X 4, Day 4 | 3 | 2 | 46 | | | | | |
| | | | | | 3 | 3 | | 75 | 72 | 99 | 88 | 88 |
| 4 | 6 | 33.50 mg/kg/dose | IP | QD X 4, Day 4 | 3 | 3 | >100 | 87 | >100 | 94 | >100 | >100 |

VEHICLES
Grp 3 –> Compound No. 6 1 (Dose = 50.00): in Saline + Tween 80 (0.05%) (Unknown) Inj Vol.: 0.1 ml/10 gm body wt
Grp 4 –> Compound No. 6 1 (Dose = 33.50): in Saline + Tween 80 (0.05%) (Unknown) Inj. Vol.. 0.1 ml/10 gm body wt

TABLE 7

| | TREATMENT | | | | | | % T/C | | | | | |
|---|---|---|---|---|---|---|---|---|---|---|---|---|
| | Compound | | | | No. of | No. of | NCI-H522 | | UACC-62 | | U251 | |
| Grp No. | No. | Dose/Units | Rt | Schedule | Mice | Fibers | IP | SC | IP | SC | IP | SC |
| 3 | 6 | 50.00 mg/kg/dose | IP | QD X 4, Day 4 | 3 | 2 | | | 99 | | | |
| | | | | | 3 | 3 | 48 | 89 | >100 | | >100 | >100 |
| 4 | 6 | 33.50 mg/kg/dose | IP | QD X 4, Day 4 | 3 | 3 | 94 | 89 | >100 | 99 | 100 | >100 |

VEHICLES
Grp 3 –> Compound No. 6 1 (Dose = 50.00): in Saline + Tween 80 (0.05%) (Unknown) Inj. Vol.: 0.1 ml/10 gm body wt
Grp 4 –> Compound No. 6 1 (Dose = 33.50): in Saline + Tween 80 (0.05%) (Unknown) Inj. Vol.: 0.1 ml/10 gm body wt Similar in vivo results also were obtained for Compound 7, which had an IP+SC score of 20 and an SC score of 8 See. Tables 8–10 below, which summarize the biological results exhibited by representative compounds of the present invention. With respect to Table 9 and superscripts (a)–(b): (a)=Values are mean+S.E. for 4 or more experiments. (b). Immune complex kinase assay. Values are mean+S.E. for 3 experiments. (c). AG-957. (d). Individual IP and SC scores and the total are shown. (e). 3 cell lines were killed

TABLE 8

CARBOXYLIC ACID MODIFICATIONS

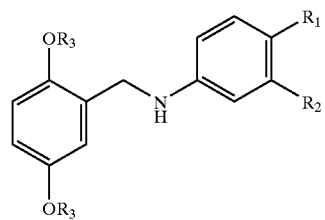

| | | | Enzyme Assays | | | | Hollow Fiber |
|---|---|---|---|---|---|---|---|
| | | | IC50 (μM)[b] | | Tumor Cell | | Assay[d] |
| R1 | R2 | R3 | IC50 (μM) 6 dMTT | p210bcl-abl in vitro phosphorylation | Mean log GI50 | Mean log TGI | Total Ip and SC Score |
| Lavendustin A | | | 44.70 + 0.93 | 41.07 + 8.93 | −4.06 | −4.00 | |
| COOH | H | H | 41.93 + 8.38 | 18.51 + 1.72 | −4.96 | −4.60 | |
| CONH2 | H | H | 20.90 + 2.34 | 4.23 + 0.73 | −4.53 | −4.26 | |
| COOCH3 | H | H | 16.63 + 0.48 | 2.90 + 0.60 | −4.95 | −4.52 | |
| COOCH(CH3)2 | H | H | 15.13 + 1.04 | 4.45 + 0.32 | −5.52 | −4.84 | 4 + 6 = 10 |
| COOH | H | CH3 | 100 + 0.3 | 50 + 0.00 | −4.0 | −4.0 | |
| COOCH3 | H | CH3 | 41.26 + 3.23 | 50 + 0.00 | −4.40 | −4.04 | |
| COOCH2Ph | H | H | 12.04 + 0.83 | 36.56 + 1.36 | −5.85 | −5.35 | 6 + 2 = 8 |
| COOCH[CH(CH3)2]2 | H | H | 9.98 + 1.32 | 11.11 + 1.11 | −5.91 | −5.35 | 4 + 2 = 6 |
| COOC(CH3)3 | H | H | 16.38 + 0.87 | 7.72 + 1.15 | −5.66 | −5.03 | 2 + 2 = 4 |
| COO-adamantyl | H | H | 9.75 + 0.81 | 13.60 + 1.81 | −6.03 | −5.44 | 8 + 8 = 16 |
| COOCH2-adamantyl | H | H | 12.84 + 0.20 | 12.62 + 1.70 | −5.89 | −5.09 | 12 + 8 = 20 |
| COOCH3 | OH | H | 17.71 + 0.11 | 6.44 + 1.78 | −5.23 | −4.70 | |
| COOCH(CH3)2 | Cl | H | 21.60 + 1.0 | 1.22 + 0.15 | −5.46 | −5.65 | 2 + 0 = 2 |
| COCH3 | H | H | 13.00 + 0.00 | 1.03 + 0.08 | −4.72 | −4.25 | |

TABLE 8-continued

CARBOXYLIC ACID MODIFICATIONS

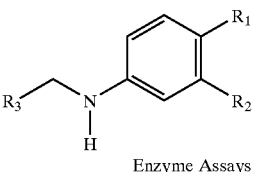

| | | | Enzyme Assays | | Tumor Cell | | Hollow Fiber Assay[d] |
| | | | IC50 ($\mu M$)[b] | | | | |
| R1 | R2 | R3 | IC50 ($\mu M$) 6 dMTT | p210bcl-abl in vitro phosphorylation | Mean log GI50 | Mean log TGI | Total Ip and SC Score |
|---|---|---|---|---|---|---|---|
| CON[CH(CH3)2]2 | H | H | 18.20 + 0.50 | 2.36 + 1.26 | −4.88 | −4.36 | |
| CH(OH)CF3 | H | H | 14.32 + 0.40 | 0.57 + 0.29 | −4.82 | −4.34 | |
| O=P(OCH3)2 | H | H | 9.83 + 0.3 | 0.49 + 0.08 | −4.61 | −4.23 | |

TABLE 9

PHENOL RING MODIFICATIONS

| | | | Enzyme Assays | | Tumor cell | | Hollow Fiber Assay[a] |
| | | | IC50 ($\mu M$)[a] 6dMTT | IC50 ($\mu M$)[b] p210bcl-abl in vitro phosphorylation | Mean log GI50 | Mean log TGI | Total Ip and SC Score |
| R1 | R2 | R3 | | | | | |
|---|---|---|---|---|---|---|---|
| COOCH3 | Cl | 2-bromo -3,6-dihydroxy-phenyl | 8.90 ± 0.50 | 3.56 ± 0.53 | −4.86 | −4.43 | |
| COOCH3 | H | 2-(1,4-dihydroxy)-naphthyl | 6.83 ± 1.68 | 50 ± 0.00 | −5.05 | −4.62 | 4 + 0 = 0 |
| COOCH3 | H | 2-(1,4-naphtoquinoyl) | 9.11 ± 1.00 | 50 ± 0.00 | −4.86 | −4.41 | |
| COOCH3 | H | 2,5-quinoyl | 15.11 ± 1.28 | 15.89 ± 2.91 | −5.60 | −4.8 | |
| COOCH3 | OH | 2,5-quinoyl | 17.00 ± 0.3 | 5.15 ± 1.01 | −4.77 | −4.36 | |
| CONH2 | H | 2,5-quinoyl | 21.74 ± 2.27 | 5.10 ± 0.30 | −4.59 | −4.31 | |
| COOCH2—C6H6 | H | 2,5-quinoyl | 22.752 ± 18 | 8.75 ± 1.25 | −5.30 | −4.78 | |
| COOCH(CH3)2 | H | 2,5-quinoyl | 17.41 ± 1.00 | 13.67 ± 5.78 | −4.57 | −4.55 | |
| COOC(CH3)3 | H | 2,5-quinoyl | 25.36 ± 1.88 | 25.88 ± 9.02 | −5.09 | −4.67 | |
| COOCH[CH(CH3)2]2 | H | 2,5-quinoyl | 38.80 ± 12.80 | 34.03 ± 9.02 | −5.25 | −4.78 | 2 + 4 = 6 |
| COOO-adamantyl | H | 2,5-quinoyl | 32 ± 0.50 | 50 ± 0.00 | −5.32 | −4.72 | |
| COC-adamantyl | H | 2,5-quinoyl | 24.80 ± 3.10 | 2.38 ± 0.45 | −5.12 | −4.60 | |
| COOC(CH3)3 | H | 6-bromo-2,5-quinoyl | 64.83 ± 1.22 | 2.68 ± 1.33 | −4.75 | −4.31 | |
| COOCH3 | Cl | 6-bromo-2,5-quinoyl | 17.50 ± 0.10 | 2.35 ± 0.41 | −4.66 | −4.34 | |
| COOCH(CH3)2 | Cl | 2,5-quinoyl | 27.70 ± 0.60 | 3.01 ± 1.75 | −5.02 | −4.41 | |

[a]Values are mean ± S.E. for 4 or more experiments.
[b]Immune complex kinase assay. Values are mean ± S.E. for 3 experiments.
[c]The IP and SC scores and total are shown.

TABLE 10

LINKER MODIFICATIONS

| | | | | Enzyme Assays | | Tumor Cell | | Hollow Fiber |
| | | | | IC50 ($\mu M$) 6dMTT | IC50 ($\mu M$)[b] p210bcl-abl in vitro phosphorylation | Mean log GI50 | Mean log TGI | Assay[c] Total Ip and SC Score |
| R1 | R2 | X-Y | R3 | | | | | |
|---|---|---|---|---|---|---|---|---|
| COOCH3 | 2,5-dihydroxyphenyl | CH2—CH2 | H | 18.47 ± 5.62 | 2.64 ± 0.99 | −5.00 | −4.43 | |
| COOCH3 | 4-bromo-2,5-dihydroxyphenyl | CH2—CH2 | H | 7.0 ± 0.50 | 4.42 ± 0.24 | −4.91 | −4.54 | 0 + 0 = 0 |
| COOH | 2,5-dihydroxyphenyl | CH2—CH2 | OH | 33.40 ± 4.80 | 12.95 ± 1.03 | −4.06 | −4.01 | |
| COOCH3 | 2,5-quinoyl | CH2—CH2 | H | 5.65 ± 0.80 | 50 ± 0.00 | −5.00 | −4.65 | 6 + 4 = 10 |
| COOCH(CH3)2 | 2,5-quinoyl | CH2—CH2 | H | 19.90 ± 0.50 | 5.26 ± 2.09 | −5.05 | −4.58 | 0 + 0 = 0 |
| COOCH(CH3)2 | 4-bromo-2,5-dihydroxyphenyl | CH2—CH2 | H | 20 ± 0.70 | 5.77 ± 0.53 | −5.12 | −4.50 | |
| COOCH3 | 4-bromo-(2,5-quinoyl) | CH2—CH2 | H | 36.50 ± 1.00 | 3.52 ± 0.16 | −4.85 | −4.43 | 0 + 0 = 0 |
| COOCH(CH3)2 | 4-bromo-(2-quinoyl) | CH2—CH2 | H | 59.80 ± 0.44 | 4.19 ± 0.07 | −4.85 | −4.48 | 0 + 0 = 0 |
| COOCH3 | 2,5-dihydoxyphenyl | CH=CH | H | 9.72 ± 0.49 | 19.86 ± 9.94 | −5.48 | −4.81 | 2 + 4 = 6 |
| COOCH3 | 2,5-quinoyl | CH=CH | H | 17.80 ± 0.22 | 5.47 ± 0.22 | −4.86 | −4.40 | 2 + 0 = 2 |
| COOH | 2,5-dihydroxyphenyl | CH=CH | OH | | | >−5.03 | >−5.0 | |

[a]Values are mean ± S.E. for 4 or more experiments.
[b]Immune complex kinase assay. Values are mean ± S.E. for 3 experiments.
[c]The individual scores and the total are shown.

V. EXAMPLES

The following examples are provided to illustrate certain features of the present invention. The invention should not be limited to the particular features exemplified.

Example 1

This example describes a general method for synthesizing compounds satisfying Formula 1 where Y is either a double bond or a single bond, and R is nitrogen. A ethanolic solution comprising 10 mmol of 2,5-dihyroxybenzaldehyde, 1 mg of NaHCO$_3$ and 15 mls ethanol is formed 4-aminoadamanlylbenzoate is then added to the solution. A solid forms and is separated from the remaining solution, washed with hexane (10 mls) and dried in vacuo to provide an imine.

A suspension of 4.29 mmol of the imine is formed, such as a suspension in about 100 milliliters of ethanol containing 50 mg of 5% Pd/C. The suspension is hydrogenated using a Parr hydrogenator for 2.5 hours, or until the reaction is complete. The reaction mixture is then filtered through celite and the pad washed with ethanol. The combined filtrates and washings are concentrated in vacuo to provide a solid. The solid is redissolved in ethanol and filtered, and the washings and filtrate again concentrated in vacuo. The solid is redissolved in ethanol and mixed with hexanes to separate the solid material. The solid material is collected by filtration, washed with hexanes and dried in vacuo to give pure amine.

Example 2

This example describes the synthesis of the following compound.

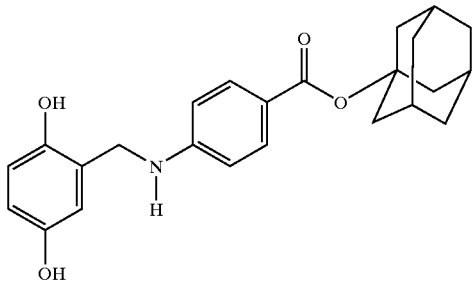

A solution of 1-adamantanol (15.2 g, 0.1 mol) in THF (100 mL) containing pyridine (25 mL) was cooled to 0–5° C. 4-nitrobenzoyl chloride (18.55 g, 0.1 mol) was added portionwise (over fifteen minutes) to this solution. The resulting slurry was stirred at 5° C. for one hour, then at room temperature for sixteen hours. The next day the reaction mixture was clarified by filtration and the solid collected. The solid was washed with EtOAc (3×20 mL). The combined filtrate and washings were concentrated in vacuo to give an oily residue. This residue was triturated with hot water (45° C.) (250 mL), shaken well, and the supernatant aqueous layer was decanted off. This was repeated twice to form a white solid, which separated from the aqueous suspension. This white solid was filtered, washed with water, and dried. This solid was dissolved in CH$_2$Cl$_2$ (200 mL) and the solution was applied to a pad of silica gel (4"×3") and eluted with CH$_2$Cl$_2$ (10×200 mL). Fractions containing pure product as indicated by TLC were concentrated in vacuo to obtain a solid (19 g). This solid was recrystallized from hot boiling EtOAc (200 mL) to give 13 g (43%) pure product.

A suspension (semi-solution) of 1-adamantyl-4-nitrobenzoate (6.1 g, 20.2 mmol) in EtOH (100 mL) containing 5% Pd/C (300 mg) was hydrogenated using a Part Hydrogenator, at 30 psi, for three hours. The reaction mixture was clarified by filtration through a celite pad, and the pad was washed with EtOH (3×25 mL). The clear colorless filtrate was concentrated in vacuo to give a residual white solid 5.3 g (96%), as a pure product.

To a solution of 1-adamantyl-4-aminobenzoate (5 g, 18.4 mmol) in EtOH (150 mL) containing $NaHCO_3$ (1 mg) was added 2,5-dihydroxybenzaldehyde (2.54 g, 18.4 mmol) and the resulting solution was stirred at room temperature for twenty hours. The next day the reaction mixture was concentrated in vacuo, to remove ~50 mL of EtOH. The residual slurry was diluted with hexane (10 mL), a yellow solid separated, was collected by filtration, washed with hexane and dried to give 6.25 g (86%) of pure product as a yellow solid.

A suspension (semi-solution) of benzoic acid, 4-[[2,5-dihydroxyphenyl)methylene]amino-1-adamantyl ester (3.27 g, 8.35 mmol) in EtOH (200 mL) containing 5% Pd/C (400 mg) was hydrogenated using a Parr Hydrogenator, at 19 psi, for one and three-quarter hours. The reaction mixture was clarified by filtration through a celite pad and the pad was washed with EtOH (3×20 mL). The combined filtrate and washings were concentrated in vacuo to give 3 g of a foamy solid. This solid was dissolved in $CH_2Cl_2$ (30 mL), and the product crystallized upon stirring. The crystalline product was filtered, washed with hexane (5×10 mL) and dried in vacuo to give 2.95 g (90%) of pure product as a light gray (beige) solid; mp 113–115° C.

In a manner substantially similar to that described in this Example 2, Compound 7 can be made by substituting 1-adamantanemethanol (which is commercially available from for example, Aldrich Chemical Co.) for 1-adamantanol.

Example 3

This example describes the synthesis of the following compound.

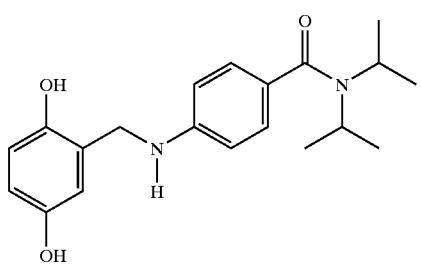

To a solution of diisopropylamine (20 g, 0.2 mol) in THF (20 mL) at 0° C., was added 4-nitrobenzoyl chloride (9.27 g, 0.05 g mol) and the reaction mixture was stirred at −5° C. for ten minutes. The cooling bath was removed and the reaction was stirred at ambient temperature for two hours. The reaction mixture was diluted with water (100 mL) and the solvent THF was removed in vacuo. The residual slurry was filtered and the solid was successively washed with $H_2O$ (10×20 mL), hexane (5×20 mL) and dried under a heat lamp (~40° C.) to give 11.8 g (94%) of product (I) as yellow crystalline solid.

A semi-solution of (I) (11 g, 43.9 mmol) in EtOH (100 mL) containing 10% Pd/C (1 g) was hydrogenated at 40 psi for one and one-half hours, using a Parr Shaker. The catalyst was removed by filtration through a celite pad and the clear colorless filtrate was concentrated in vacuo to give a white residual solid. This solid was reprecipitated from its solution in $CH_2Cl_2$, by adding hexane. The solid was collected by filtration, washed with hexane and dried in vacuo to give 9.2 g (98%) of product (II) as a white solid.

A solution of (II) (3.19 g, 14.4 mmol) and 2,5-dihydroxybenzaldehyde (2 g, 14.4 mmol) in ethanol (40 mL) containing $NaHCO_3$ (10 mg) was stirred at room temperature under Ar for sixteen hours. The following day ~20 mL of EtOH was removed from the reaction mixture in vacuo, and the residual slurry was diluted with hexane (50 mL) and the yellow solid was collected by filtrations, washed with hexane (5×10 mL) and dried in vacuo to give 4.8 g (97%) of product (III) as a yellow solid.

To a cold (−10° C.) solution of (III) (2 g, 5.87 mmol) in a mixture of MeOH (100 mL) and THF (10 mL) was added $NaBH_4$ (0.6 g, 16 mmol) and the mixture was stirred at 10° C. until the initial yellow solution turned colorless. The reaction mixture was diluted with degassed water (20 mL) and the volatiles were removed in vacuo. The residual slurry (~20 mL) was diluted with water (50 mL) and stirred vigorously. The solid was collected by filtration, washed with water (5×10 mL), followed by hexane (5×10 mL) and dried in vacuo to give 1.53 g (76%) of product (III). This was dissolved in a mixture of EtOAc (5 mL) and MeOH (5 mL) and the solution was applied to a silica gel pad (5×10 cm) and eluted with $CH_2Cl_2$ (1 L). Appropriate factions were combined and the solvent was removed in vacuo to give a residual solid which was recrystallized from $CH_2Cl_2$ (20 mL) to give 750 mg of pure product (IV) as a white solid, mp 168–170° C.

Example 4

This example describes the synthesis of the following compound

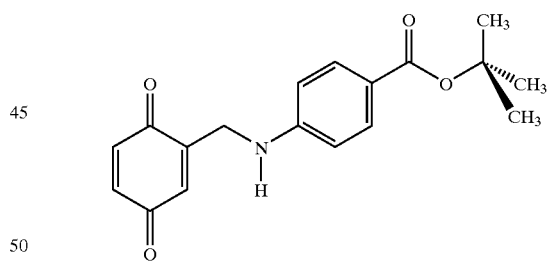

To stirred tert-butanol (room temperature, argon) (50 mL) was added a solution of η-BuLi (2.5M in hexane, 14 mL; 0.035 mol) dropwise at such a rate as to maintain the internal temperature at 25–30° C. After the addition was complete, the reaction mixture was stirred for thirty more minutes. A solution of 4-nitrobenzoyl chloride (6.50 g; 0.035 mol) in $Et_2O$ (50 mL) was added dropwise over one hour to the above reaction mixture, maintaining the internal temperature at 30° C. After the addition was complete, the reaction mixture was stirred at ambient temperature for two hours, then diluted with ice cold $H_2O$ (20 mL). The organic phase was separated and the aqueous phase was extracted with $Et_2O$ (2×100 mL). The combined organic phase was washed with saturated aqueous NaCl, dried ($MgSO_4$), and concentrated in vacuo to give a solid (7.5 g). This solid was recrystallized (twice) from Et$_2$O (40 mL) to give 2.4 g (31%) of purified material suitable for further transformation. Additional reactions were carried out to give a total of 5 g of similar product.

A solution of t-butyl-4-nitrobenzoate (2.30 g; 0.0103 mol) in MeOH (100 mL) containing 5% Pd/C (300 mg) was hydrogenated at 30 psi and room temperature for three hours. The catalyst was removed by filtration (celite pad), and the filtrate was concentrated in vacuo to give 1.9 g (90%) of desired product suitable for further transformation. Additional reactions were carried out to give a total of ~4.2 g of similar material.

The reaction mixture, containing 2,5-dihydroxybenzaldehyde (1.38 g; 0.01 mol) and compound t-butyl-4-aminobenzoate (1.90 g, 0.01 mol) in EtOH (25 mL) was stirred (ambient temperature, argon) for twenty-four hours. The reaction mixture was diluted with hexane (20 mL) and stirred for fifteen minutes. The bright orange precipitate was collected by filtration, washed on the filter with hexane, and dried in vacuo at room temperature to give 1.6 g (52%) of desired product suitable for further transformation. Additional reactions were carried out to give a total of 2.5 g of similar material.

A solution of benzoic acid 4-[[2,5-dihydroxyphenyl)methylene)amino]-t-butyl ester (1.50 g; 0.0048 mol) in EtOH (100 mL) containing 5% Pd/C (400 mg), was hydrogenated at 10 psi and room temperature for three hours. The catalyst was removed by filtration (celite pad and the filtrate was concentrated in vacuo to give 1.5 g (100%) of a crude material as a dark solid. This solid was dissolved in Et$_2$O (15 mL), and the solution was diluted with hexane (50 mL). The resulting suspension was stirred at ambient temperature for thirty minutes. The solid that separated was collected by filtration, washed on the filter with hexane and dried in vacuo to give 13 g (87%) of partially purified product. This material was applied to a silica gel (50 g) column and eluted with hexane:EtOAc (5.3) The appropriate (by TLC evaluation) fractions were combined, and the solvent was removed in vacuo to give 950 mg (63%) of purified product as a beige solid, mp. 158–160° C. Additional reactions were carried out to give a total of 21 g of similar material.

Air was bubbled, through a solution of 4-[[2,5-dihydroxyphenyl)methyl)amino]-t-butyl ester (1 g, 3.17 mmol) in MeOH (100 mL) containing salcomine hydrate (300 mg), for two hours The reaction mixture was concentrated in vacuo to obtain a dark solid. This solid was taken in EtOAc (250 mL) and clarified by filtration. The filtrate was washed successively with H$_2$O, brine, dried (MgSO$_4$) and concentrated in vacuo to give a dark solid (1 g). This was presorbed on a gram of silica from a EtOAc solution, this was applied to a silica gel column, and the column was eluted with EtOAc/hexane (3:5). Fractions containing pure product as indicated by TLC were combined and concentrated in vacuo to give a red residue (557 mg). This residue was dissolved in CH$_2$Cl$_2$ (5 mL) and the solution was diluted with hexane (70 mL). The resulting suspension was stirred for twenty minutes, the solid was filtered, washed with hexane and dried in vacuo to give 438 mg (43%) of pure product as a red solid, mp 125–127° C.

Example 5

This example describes the synthesis of the following compound.

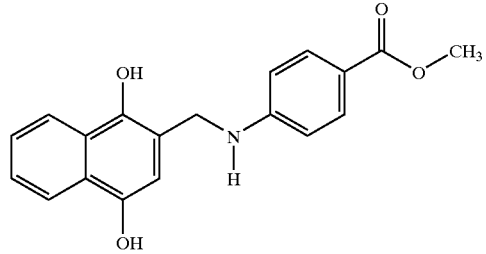

A mixture of 1,4-naphthoquinone (40.0 g, 0.253 mol) and 10% Pd/C (0.4 g) was shaken under H$_2$ (50 psig) for six hours. The catalyst was removed by filtration, and the filter pad was washed with degassed MeOH (2×25 mL). The filtrate was spin-evaporated in vacuo to a solid, then further dried using a mechanical pump to give 40.5 g (100%) of product suitable for further transformation.

A mixture of 1.4-dihydroxynaphthalene (40.5 g, 0.253 mol), 3,4-dihydro-2H-pyran (106.7 g, 1.268 mol), and p-toluenesulfonic acid monohydrate (0.48 g) in degassed CH$_2$Cl$_2$ (960 mL) was stirred at 25° C. for sixteen hours The mixture was diluted with Et$_2$O (1.2 L), washed in succession with saturated aqueous NaHCO$_2$ (400 mL), H$_2$O (400 mL), brine (400 mL), dried over MgSO$_2$, and spin-evaporated in vacuo to an oil The oil was chromatographed on a silica gel column (2.0 kg), packed in and eluted with CH$_2$Cl$_2$ (20.0 L). Appropriate fractions as determined by TLC were combined and spin-evaporated in vacuo to give 31.5 g (37.9%) of product as a viscous oil. Additional reactions were performed to gave a total of 810 g of product suitable for further transformation.

To a stirred, argon blanketed mixture of η-BuLi (1.6M in hexanes) (94.5 mL, 151.2 mmol), Et$_2$O (180 mL) and hexanes (280 mL) was added a solution of 1,4-bis (tetrahydropyranyloxy)naphthalene (31.5 g, 95.9 mmol) in Et$_2$O (220 mL) (rapidly), dropwise over twenty minutes. The resulting mixture was stirred at 25° C. for one-half hour, then heated at reflux for one hour. The mixture was cooled (25° C.), and DMF (11.7 mL, 151.2 mmol) was added (rapidly), dropwise. The resulting mixture was stirred at 25° C. for two hours, then quenched with ice/H$_2$O (500 mL). Two layers were separated, and the aqueous layer was extracted with Et$_2$O (3×200 mL). The combined organic layers were washed with brine (200 mL), dried over MgSO$_2$ (10 g) and concentrated in vacuo to a slurry. The slurry was diluted with hexanes (100 mL). The solids were collected by filtration and dried to constant weight in vacuo to give 22.4 g (65.5%) of pure product. Additional reactions were performed to give a total of 35.8 of material suitable for further transformation.

A degassed mixture of HOAc (100 mL), THF (50 mL), H$_2$O (25 mL) and 1,4-bis(tetrahydropyranyloxy)-2-naphthaldeyhyde (5.0 g, 14.0 mmol) was heated at 45° C. under argon for three hours. The mixture was poured into degassed H$_2$O (1.0 L). The resulting precipitate was collected by filtration, washed with H$_2$O (2×100 mL) and hexanes (2×100 mL), then dried to constant weight in vacuo to give 2.4 g (92.3%) of product suitable for further transformation.

An argon-blanketed mixture of 1,4-dihydroxynaphthaldeyhyde (2.3 g, 12.2 mmol), Na$_2$CO$_3$ (~3 mg), and methyl 4-aminobenzoate (1.9 g, 12.3 control) in EtOH (150 mL) was stirred at 25° C. for seventy-two hours. The resulting suspension was diluted with hexanes (150 mL) and stirred for fifteen minutes. The precipitate was collected by filtration, washed with hexanes (2×25 mL) and dried to constant weight in vacuo to give 1.3 g (33.3%) of product suitable for further transformation.

To a cold (0° C.), argon-blanketed suspension of benzoic acid, 4-[[2-(1,4-dihydroxynaphthalenyl)methylene]-amino-, methyl ester (1 g, 3.1 mmol) in MeOH (30 mL) was added NaBH, (300 mg, 7.9 mmol) in one portion. The mixture was stirred for fifteen minutes, then diluted with degassed H₂O (60 mL), and acidified with concentrated HCl ((~1 mL). The mixture was then neutralized to pH ~6.5 with saturated aqueous NaHCO₃ (~10 mL). The resulting precipitate was collected by filtration, washed with degassed H₂O (3×20 mL) and dried to constant weight in vacuo at 40° C. to give 874 mg (87%) of pure product (VI) as a tan solid. mp 135–137° C. (decomposes).

Example 6

This example describes the synthesis of the following compound

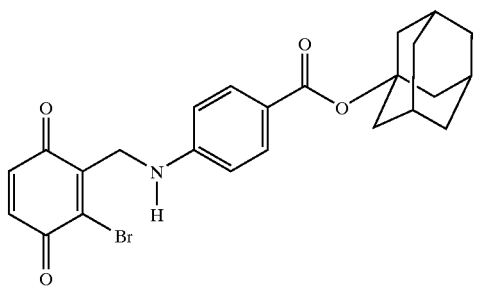

A solution of 1-adamantanol (15.2 g, 0.1 mol) in THF (100 mL) containing pyridine (25 mL) was cooled to 0–5° C. 4-nitrobenzoyl chloride (18.55 g, 0.1 mol) was added portionwise (over fifteen minutes) to this solution. The resulting slurry was stirred at 5° C. for one hour, then at room temperature for sixteen hours. The next day the reaction mixture was clarified by filtration, the solid collected and washed with EtOAc (3×20 mL). The combined filtrate and washings were concentrated in vacuo to give an oily residue. This residue was triturated with hot water (45° C.) (250 mL), shaken well, and the supernatant aqueous layer was decanted off. This was repeated, and a white solid separated from the aqueous suspension. This solid was filtered, washed with water, and dried. This solid was dissolved in CH₂Cl₂ (200 mL) and the solution was applied to a pad of silica gel (4"×3") and eluted with CH₂Cl₂ (10×200 mL). Fractions containing pure product as indicated by TLC were concentrated in vacuo to obtain a solid (19 g). This solid was recrystallized from hot boiling EtOAc (200 mL) to give 13 g (43%) of pure product.

A suspension (semi-solution) of adamantyl-4-nitrobenzoate (6.1 g, 20.2 mmol) in EtOH (100 mL) containing 5% Pd/C (300 mg) was hydrogenated using a Parr Hydrogenator, at 30 psi, for three hours. The reaction mixture was clarified by filtration through a celite pad, and the pad was washed with EtOH (3×25 mL). The clear colorless filtrate was concentrated in vacuo to give a residual white solid 5.3 g (96%), as a pure product.

To a stirred solution of 2,5-dihydroxybenzaldehyde (2.00 g; 14.5 mmol) in CHCl₃ (90 mL) at room temperature and under an argon atmosphere was added a solution of Br₂ (2.31 g, 14.5 mmol) in CHCl₃ (60 mL) dropwise over one hour. Upon completion of the addition, the reaction mixture was stirred for one hour, then diluted with CH₂Cl₂ (350 mL). The resulting solution was washed by stirring for twenty minutes with saturated aqueous NaHCO₃, dried (MgSO₄), and concentrated in vacuo to give a bright yellow solid 2.5 g (79%) suitable for further transformation.

To a solution of 1-adamantyl-4-aminobenzoate (1.25 g, 4.61 mmol) in EtOH (10 mL) containing NaHCO₃ (1 mg) was added 2-bromo-3,6-dihydroxybenzaldehyde (1.0 g. 4.61 mmol) and the resulting solution was stirred at room temperature for twenty hours. The next day the reaction mixture was diluted with hexane (30 mL), the orange solid collected by filtration, washed with hexane and dried to give 1.0 g of pure product as a solid. The filtrate was concentrated to give 550 mg of additional material.

To the semi-solution of benzoic acid, 4-[[(2-bromo-3,6-dihydroxyphenyl)methylene]-amino]-1-adamantyl ester (1.2 g, 2.55 mmol) in MeOH (100 mL) at 10° C. was added NaBH₄ (0.5 g, 13.2 mmol) over ten minutes. The reaction mixture changed from red to colorless. The reaction mixture was stirred for thirty minutes and diluted with degassed H₂O (50 mL). The reaction mixture was concentrated in vacuo to remove most of the methanol. The residual slurry (~50 mL) was extracted with CH₂Cl₂, (110 mL) and EtOAc (50 mL). The combined organic extracts were washed with brine (50 mL), dried (Na₂SO₄) and concentrated in vacuo to give 1.2 g of the residual off-pink solid. This was used in the next reaction without further purification.

Air was bubbled through a stirred solution of benzoic acid, 4-[[(2-bromo-3,6-dihydroxyphenyl)methyl]-amino]-1-adamantyl ester (1.2 g, 2.55 mmol) in MeOH (100 ml) in presence of salcomine hydrate (300 mg), at room temperature for two hours. The reaction mixture was concentrated in vacuo to give a dark purple solid. This solid was dissolved in CH₂Cl₂, (25 mL), the solution applied to a silica gel column (2×20 cm), and the column eluted with CH₂Cl₂, (2 L). The appropriate fractions were combined, and the solvent removed in vacuo to leave 830 mg of purified material. This material was triturated with CH₂Cl₂ (5 mL) and diluted with hexane (20 mL). The purple solid that separated was filtered, washed with hexane and dried in vacuo at −40° C. to give 710 mg of pure product (VI) as a red crystalline powder, mp 156–158° C. (decomposes).

Example 7

This example describes the synthesis of the following compound

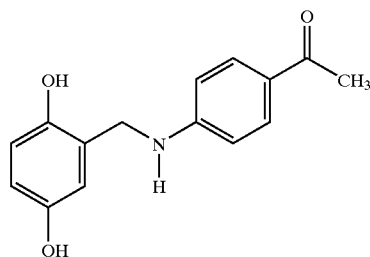

A mixture comprising 2,5-dihydroxybenzaldehyde (1.50 g; 10.9 mmol), 4-aminoacetophenone (1.47 g; 10.9 mmol), and NaHCO₃ (~10 mg) in EtOH (40 mL) was stirred at ambient temperature and under an argon atmosphere for eighteen hours. The reaction mixture was concentrated in vacuo to leave 2.7 g (97%) of product (I) as a yellow solid, which was used for the next step without further purification.

A solution of compound acetophenone, 4'-[[dihydroxyphenyl)methylene]-amino (0.50 g; 1.96 mmol) in EtOH (150 mL), in presence of the catalyst 5% Pd/BaCO$_3$ (250 mg), was hydrogenated at 15 psi and room temperature for two hours. The catalyst was removed via filtration and discarded. The filtrate was concentrated in vacuo to ~10 mL of volume and diluted with hexane (250 ml). The resulting suspension was stirred at room temperature for twenty minutes, the precipitate collected by filtration, washed with hexane, and dried in vacuo at room temperature to give 470 mg (93%) of product, mp 194° C. (decomp.); 197–199° C. melt.

Example 8

This example describes the synthesis of the following compound.

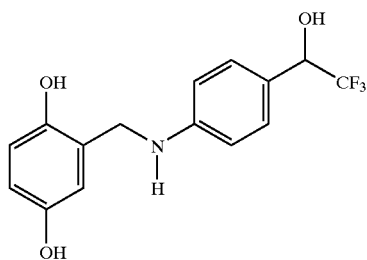

To a stirred mixture of 4-nitrobenzaldehyde (6.3 g, 41.7 mmol) and trimethyl (trifluoromethyl) silane (0.5M in THF) (100 mL, 50 mmol) was added tetrabutylammonium fluoride (1.0M in THF) (316 μL, 0.316 mmol). The resulting mixture was stirred at 25° C. for one hour. To the reaction mixture was added 1.0M HCl (300 mL), and the reaction mixture was stirred for three hours. The reaction mixture was extracted with Et$_2$O (2×500 mL) and the combined ether extracts were dried (MgSO$_4$) and concentrated in vacuo to give 9.2 g (100%) of product as a residual solid.

A solution of benzenemethanol, 4-nitro-α-(trifluoromethyl) (1.5 g, 6.78 mmol) in ethanol (50 mL) containing 5% Pd/C (300 mg) was hydrogenated using a Parr Apparatus at 22 psi for two hours. The catalyst was removed by filtration (through a celite pad) and the clear filtrate was concentrated in vacuo to give a residual solid. This solid was dissolved in CH$_2$Cl$_2$ (10 mL) and hexane (100 mL) was added with stirring. The solid that precipitated was collected by filtration and dried in vacuo to give 1.2 g of product (II).

A solution of benzenemethanol. 4-amino-α-(trifluoromethyl) (1 g, 5.23 mmol) and 2,5-dihydroxybenzaldehyde (0.73 g, 5.23 mmol) in ethanol (10 mL) containing NaHCO$_3$ (5 mg) was stirred for sixteen hours at room temperature. The resulting dark red reaction mixture was concentrated in vacuo to a volume of ~3 mL and diluted with hexane (50 mL) while stirring vigorously. After fifteen minutes, the precipitated solid was collected by filtration, washed with hexane and dried in vacuo to give 1.6 g of product.

A solution of benzenemethanol, 4-[[2,5-dihydroxyphenyl)methylene]-amino-α-(trifluoromethyl) (1.5 g, 4.82 mmol) in ethanol (70 mL) containing 10% Pd/C (200 mg) was hydrogenated at 20 psi for one and one-half hours using a Parr Apparatus. The catalyst was removed by filtration (through a celite pad) and the clear filtrate was concentrated in vacuo to give a gummy brown solid. This solid was triturated with EtOH (1.5 mL) and CH$_2$Cl$_2$, (100 mL) was added. To this solution was added hexane (10 mL) and the resulting solution was concentrated in vacuo at −5° C., to a volume of ~35 mL. The crystalline solid that separated was collected by filtration washed with hexane and dried in vacuo to give 1.17 g (78%) of pure product as a beige solid. mp 118–120° C.

Example 9

This example describes the synthesis of the following compound.

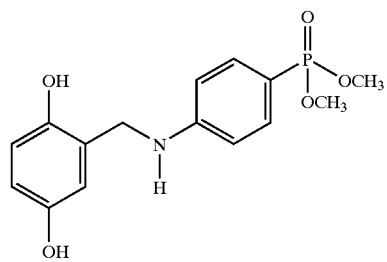

A stirred solution of 4-iodoaniline (10.0 g, 0.46 mol) in trimethyl phosphate (250 mL; 263 g; 2.12 mol), under argon was irradiated for twenty hours at 0° C. The reaction mixture was concentrated in vacuo to give the crude product as an oil (17.5 g). This oil was purified on a 500 g silica gel column, packed and eluted with EtOAc. The appropriate fractions were combined, and the solvent was removed in vacuo to leave 3.0 g of the product as a semi solid This material contained trimethyl phosphate as an impurity (30%, based on $^1$H NMR). This material was used in the next step without any further purification.

A mixture of 2,5-dihydroxybenzaldehyde (0.96 g, 6.96 mmol) and phenylphosphonic acd, 4-[[(2,5-dihydroxyphenyl)methylene]-amino]-, dimethyl ester (2.0 g of 70%, 6.96 mmol) in EtOH (40 mL) was stirred at ambient temperature under argon for twenty hours. The reaction mixture was concentrated in vacuo to a volume of ~10 mL. The residue was diluted with hexane (200 mL), the resulting suspension was stirred for fifteen minutes, the orange precipitate was collected by filtration, washed with hexane, and dried in vacuo to constant weight to give 2.2 g (100%) of the product.

A solution of 2,5-dihydroxybenzaldehyde (0.96 g, 6.96 mmol) and phenylphosphonic acd. 4-[[(2.5-dihydroxyphenyl)methylene]-amino] (2.0 g; 6.2 mmol) in EtOH (200 mL) containing 5% Pd/C (400 mg) was hydrogenated at 15 psi for two hours. The catalyst was removed via filtration, and the filtrate was concentrated in vacuo to an oil, which crystallized upon standing at room temperature (1.5 g). This maternal was dissolved in a mixture of EtOAc (10 mL) and MeOH (2 mL). The resulting solution was diluted with hexane (150 mL) and stirred for fifteen minutes. The precipitate that formed was isolated by filtration, washed with hexane and dried in vacuo to constant weight to give 1.35 g of pure product, mp. 140–142° C.

Example 10

This example describes the procedure used for cell culture and growth assays. Human leukemia, Philadelphia-chromosome-positive CML cell line K562 was obtained from ATCC (Rockville, Md.). Cells were cultured in RPMI medium containing 10% fetal calf serum, 2 mM glutamine, 100 units/ml of penicillin and 100 μg/ml streptomycin Cells ($2 \times 10^3$ cells/well) were incubated with increasing concentrations of compounds of the present invention dissolved in DMSO in a final volume of 200 μl in 96-well plates. Control cells were incubated with medium containing identical concentrations of the DMSO solvent. Growth of K562 cells was quantitated after 6 days by ability of living cells to reduce the yellow dye 3-(4,5-dimethylthiazolyl)-2,5-diphenyltetrazolium bromide (MTT) to a blue formazan product. Further information concerning this procedure is provided by Mossman T., "Rapid Colorimetric Assay for Cellular Growth and Survival—Application to Proliferation and Cytotoxicity Assays," *J. Immunol. Methods* 1983, 65:55–63, which is incorporated herein by reference.

Example 11

Inhibition of in vitro auto-phosphorylation of $p210^{bcr-abl}$ in immune-complex kinase assays were conducted as follows. K562 cell line cells were washed twice in phosphonate-buffered saline. The washed cells were lysed in PLC lysis buffer 150 mM HEPES (pH 7.5), 150 mM NaCl, 10% (v/v) glycerol, 1% (v/v) Triton X-100, 1.5 mM MgCl$_2$, 1 mM EGTA. 10 μg/ml leupeptin, 10 μg/ml aprotinin, 1 mM sodium orthovanadate. 10 mM sodium pyrophosphate, 100 mM sodium fluoride and 1 mM phenylmethyl sulfonyl fluoride| Cell lysates were centrifuged at 100,000 g for 15 minutes and the supernatant collected. Protein concentrations of the clarified supernatants were determined by the Bradford Protein Assay, and the same quantity of protein was immunoprecipitated from control (vehicle-treated) and drug-treated cells. Cell lysates were incubated and gently rocked at 4° C. for 4 hours overnight with antibodies. Immune complexes were collected by incubation with Protein A-Sepharose beads (Pharmacia, Piscataway N.J.) and immune complexes (beads) were washed three times with HNTG buffer [20 mM HEPES (pH 7.5), 10% glycerol, 0.1% Triton X-100, 150 mM NaCl and 1 mM sodium orthovanadate] to remove unbound material. Bound proteins were boiled for 5 minutes in 2×SDS sample buffer (63 mM Tris-HCl, ph 6.8; 10% glycerol; 2% SDS; 0.0025% bromophenol blue: and 0.72 mM 2 mercaptoethanol) prior to SDS-PAGE. Proteins were resolved on 4–20% gradient mini gels from Novex Experimental Technology (San Diego, Calif.).

After SDS-PAGE, proteins were electrophoretically transferred onto Immobilon polyvinylidene difluoride (PVDF) membranes (Millipore, Bedford, Mass.) at 250 mA for 4 hours at 4° C. using 2× Tris glycine transfer buffer (50 mM Tris, glycine), 20% methanol and 0.1% SDS. Residual binding sites on the membrane were blocked by incubation in TTS (20 mM Tris pH 7.4, 0.9% NaCl and 0.05% Tween 20) containing 3% BSA overnight at 4° C. or for 4 hours at room temperature. Blots were incubated for 1–1.5 hours with TTS containing 0.3% BSA with 1 μg/ml of mouse anti-P-Tyr, 2 μg/ml of mouse anti-Grb2 or 1 μg/ml of rabbit anti-Shc antibody. Blots were washed three times for 6 minutes each with TTS containing 0.3% BSA and probed with a 1:1000 dilution of rabbit anti-mouse antibody or directly with [$^{125}$I]Protein A (Amersham, Arlington Heights, Ill.) in blocking solutions. Proteins were visualized by autoradiography (exposed for 1–2 days at −70° C.).

The $p210^{bcr-abl}$, protein immunoprecipitates were washed twice with HTNG buffer Immunoprecipitates were washed once with 50 mM Tris (pH 7.0) and distributed to each reaction in 20 μl of 20 mM PIPES [piperazine-N,N'-bis(ethanesulfonic acid)] (pH 7.0)–20 mM MnCl$_2$. Then, 10 μl of compounds made according to the present invention at desired concentrations from working stock solution prepared in 20 mM PIPEs (pH 7.0)–20 mM MnCl$_2$ were added to each reaction tube. Reactions were initiated with the addition of 10 μl of [γ-$^{33}$P]ATP (10 μCi per sample, 3000 Ci/mmol; Amersham), incubated for 20 minutes at 30° C., stopped by addition of 10 μl of 5×SDS sample buffer, heated at 100° C. for 5 minutes, and analyzed on 4–20% SDS-PAGE and by autoradiography.

To assess the effect of drugs added in vitro on the state of $p210^{bcr-abl}$ in the immune complexes, K562 cells were labeled with $^{32}$P, lysed in PLC buffer and immune complexes containing $^{32}$P-labeled $p210^{bcr-abl}$ were collected on protein Sepharose beads and beads were washed four times with HNTG buffer. Immune complexes were divided into several tubes in 30 μl of PLC buffer in the presence of compounds made as described herein.

Example 12

This example describes the method used for in vivo testing of mice. Human cancer cells were cultivated in polyvinylidene fluoride (PVDF) hollow fibers. A sample of each cancer cell line was implanted intraperitoneally and subcutaneously in mice. Each mouse received a total of 6 fibers, 3 intraperitoneally and 3 subcutaneously, representing 3 distinct cancer cell lines. Three mice were treated with compounds made according to the present invention at each of two test doses intraperitoneally using a QD×4 treatment schedule. Vehicle controls consisted of 6 mice receiving the compound diluent only The fiber cultures were collected on the day following the last treatment. Anticancer effects were assessed by determining viable cell mass for each of the coil line using a formazan dye (MTT) conversion assay. From this, the % TIC was calculated using the average optical density of the compound-treated samples divided by the average optical density of the vehicle controls. In addition, the net increase in cell mass was determined for each sample as samples of fiber cultures were assessed for viable cell mass on the day of implantation into mice. This allowed cytostatic and cytocidal capacities of these compounds to be assessed.

Example 13

This example describes a method for treating humans with the compounds of the present invention. Compounds satisfying Formulas 1 and/or 2 are obtained. These compounds are then administered orally or intravenously to humans at a dose of from about 30 mgs/kg of subject/dose to about 50 mgs/kg of subject/dose, or to provide a total amount of compound or compounds to the subject per treatment of from about 0.1 gram to about 3 grams.

Alternatively, compositions comprising one or more compounds satisfying Formula 1 or 2, and at least one material selected from the group consisting of men carriers, excipients, diagnostics, direct compression binders, buffers, stabilizers, fillers, disintegrants, flavors, colors, lubricants, other active ingredients, other materials conventionally used in the formulation of pharmaceutical compositions, or mixtures thereof, are administered orally or intravenously to humans. The compositions are administered to provide a total amount of compound or compounds to the subject of from about 30 mgs/kg of subject/dose to about 50 mgs/kg of subject/dose, or a total amount of compound or compounds per dose of from about 0.1 gram to about 3 grams.

The present invention has been described with respect to certain preferred embodiments, but should not be limited to the particular features described. Instead, the scope of the invention should be determined by the following claims.

We claim:

1. A compound having an in vivo biological activity of 4 or greater as measured by an IP+SC score, the compound satisfying Formula 1

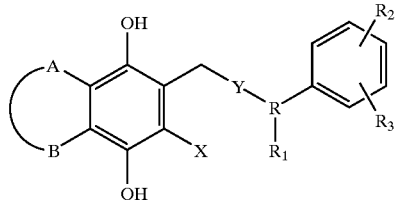

Formula 1 where both A and B are hydrogen, X is either hydrogen or halogen, Y is a single bond and $R_1$ is hydrogen, $R_2$ is selected from the group consisting of aliphatic groups having from about 3 to about 16 carbon atoms, aliphatic alcohols having from about 3 to about 16 carbon atoms, aliphatic amides having from about 3 to about 16 carbon atoms, aliphatic esters having from about 3 to about 16 carbon atoms, aliphatic ketones having from about 3 to about 16 carbon atoms, and aliphatic phosphonic acid esters, and $R_3$ is either ortho, meta or para with respect to R, and is selected from the group consisting of hydrogen, hydroxyl and halogen when at least one of A, B or X is other than hydrogen, and from the group consisting of hydrogen and halogen when A, B and X are hydrogen, or Formula 2

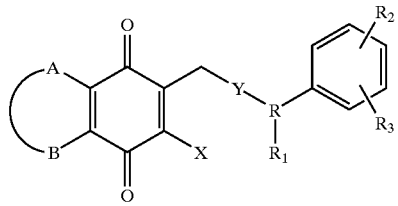

Formula 2 where A and B independently are selected from the group consisting of hydrogen and halogen, or both are carbon atoms in an aromatic ring, X is either hydrogen or halogen, Y is either a single bond or a double bond, R is either carbon or nitrogen, $R_1$, is hydrogen or an aliphatic group having from about 1 to about 30 carbon atoms, $R_2$ is meta or para to R and is selected from the group consisting of amino, aliphatic amine, aliphatic alcohols, aliphatic amides, aliphatic esters, aliphatic ketones and phosphonic acid esters with the aliphatic groups comprising from about 1–30 carbon atoms, and $R_3$ is either ortho, meta or para to R and is selected from the group consisting of hydrogen, hydroxyl and halogen.

2. The compound according to claim 1 wherein $R_2$ is para to R.

3. The compound according to claim 1 where $R_2$ is para to R and is selected from the group consisting of lower alkyl esters, adamantyl esters, adamantylalkyl esters, adamantylamino, adamantylalkylamino, lower alkyl alcohols, lower haloalkyl alcohols, lower alkyl amides, lower alkyl ketones and aliphatic phosphonic acid esters.

4. The compound of claim 1 where $R_2$ is selected from the group consisting of adamantyl ester, —$CH_2$adamantyl ester, isopropyl ester, t-butyl ester, diisopropyl amide, trifluoromethylisopropy alcohol, and aliphatic phosphonic acid ester.

5. The compound according to claim 1 where compound selected from the group consisting of 4'-adamantylbenzoate-1'-N-2,5-dihydroxybenzylamine, 4'-adamantylmethylbenzoate-1'-N-2,5-dihydroxybenzylamine, 5'-chloro-4'-isopropylbenzoate-1'-N-2,5-dihydroxybenzylamine, 4'-(trifluoromethylethanol)-1'-N-2,5-dihydroxybenzylamine, 4'-phenylphosphonate-1-N-2,5-dihydroxybenzylamine, 4'-isopropylbenzoate-1'-N-5-bromo-2,5-dihydroxybenzylamine, 4'-chloro-5'-methylbenzoate-1'-N-3-bromo-2,5-dihydroxybenzylamine, 5'-hydroxy-4'-methylbenzoate-1'-N-5-bromo-2,5-dihydroxybenzylamine, 4'-t-butylbenzoate-1'-N-2,5-dihydroxybenzylamine, and 4'-diisopropylbenzamide-N-2,5-dihydroxybenzylamine.

6. The compound according to claim 1 having the structural formula

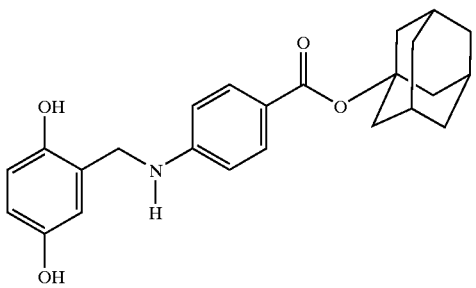

7. A compound according to Formula 1

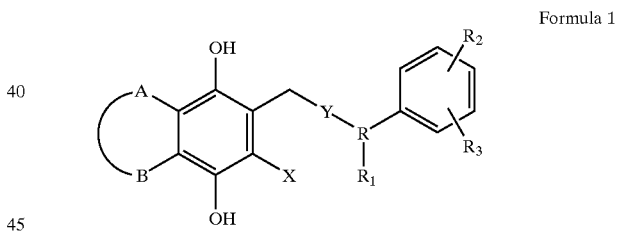

Formula 1 where A and B independently are selected from the group consisting of hydrogen and halogen, or are carbon atoms in an aromatic ring, X is either hydrogen or halogen, Y is a single bond or a double bond, R is carbon or nitrogen, $R_1$ is hydrogen or an aliphatic group, $R_2$ is either meta or para to R, is sufficiently bulky to maintain in vivo biological activity, and is selected from the group consisting of amino, aliphatic amines, aliphatic alcohols, aliphatic amides, aliphatic phosphonic acid esters, the aliphatic groups comprising from 1 to about 30 carbon atoms, aliphatic esters having from 3 to about 30 carbon atoms and aliphatic ketones having from 3 to about 30 carbon atoms, and $R_3$ is either ortho, meta or para with respect to R, and is selected from the group consisting of hydrogen, hydroxyl and halogen when at least one of A, B or X is other than hydrogen, from the group consisting of hydroxyl and halogen when $R_2$ is an amino group para to R and A, B and X are hydrogen, and from the group consisting of hydrogen and halogen when A, B and X are hydrogen, or Formula 2

Formula 2

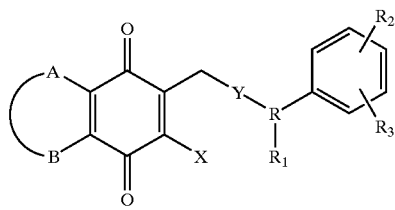

where A and B independently are selected from the group consisting of hydrogen and halogen, or both are carbon atoms in an aromatic ring, X is either hydrogen or halogen, Y is either a single bond or a double bond, R is either carbon or nitrogen, $R_1$ is hydrogen or an aliphatic group having from about 1 to about 30 carbon atoms, $R_2$ is meta or para to R and is selected from the group consisting of amino, aliphatic amine, aliphatic alcohols, aliphatic amides, aliphatic esters, aliphatic ketones and phosphonic acid esters with the aliphatic groups consisting of from about 1–30 carbon atoms, and $R_3$ is either ortho, meta or para to R and is selected from the group consisting of hydrogen, hydroxyl and halogen;

where, with respect to Formula 1, $R_2$ includes a carbonyl.

8. The compound according to claim 7 where, with respect to Formula 1, $R_2$ includes a carbonyl and is substituted immediately adjacent the carbonyl carbon.

9. The compound according to claim 7, where $R_2$ is substituted at a position one or two atoms removed from the carbonyl.

10. A compound according to Formula 1

Formula 1

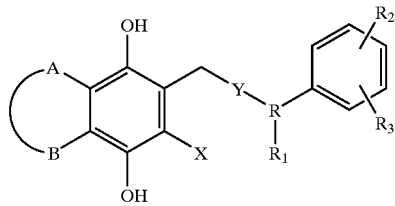

where A and B independently are selected from the group consisting of hydrogen and halogen, X is either hydrogen or halogen, Y is a single bond, R is nitrogen, $R_1$ is hydrogen, $R_2$ is para to R and is selected from the group consisting of adamantyl ester, —CH$_2$adamantyl ester, isopropyl ester, t-butyl ester, diisopropyl amide, trifluoromethylisopropyl alcohol and aliphatic phosphonic acid ester and $R_3$ is either ortho or meta to R and is selected from the group consisting of hydrogen, hydroxyl and halogen, or Formula 2

Formula 2

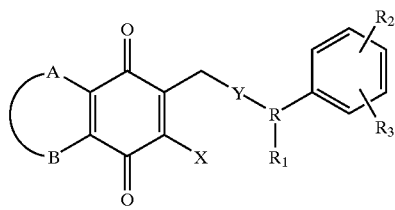

where A and B independently are selected from the group consisting of hydrogen and halogen, X is either a hydrogen or halogen atom, Y is a single bond, R is nitrogen, $R_1$ is hydrogen, $R_2$ is para to R and is selected from the group consisting of adamantyl ester, —CH$_2$adamantyl ester, iso-propyl ester, methyl ester, t-butyl ester, and $R_3$ is either ortho or meta to R, and is selected from the group consisting of hydrogen, hydroxyl and halogen.

11. A pharmaceutical composition, comprising:

an amount of a compound effective to inhibit the proliferation of cells in a subject, the compound having an in vivo biological activity of 4 or greater as measured by an IP+SC score, the compound satisfying Formula 1

Formula 1

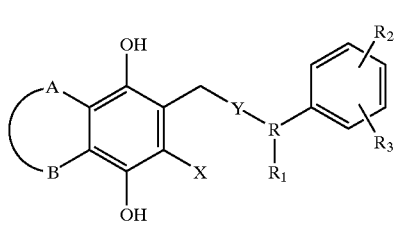

where A and B independently are selected from the group consisting of hydrogen and halogen, X is either hydrogen or halogen, Y is a single bond, R is nitrogen, $R_1$ is hydrogen, $R_2$ is para to R and is selected from the group consisting of adamantyl ester, —CH$_2$adamantyl ester, isopropyl ester, t-butyl ester, diisopropyl amide, trifluoromethylisopropyl alcohol and aliphatic phosphonic acid ester, and $R_3$ is either ortho or meta to R and is selected from the group consisting of hydrogen, hydroxyl and halogen, and/or a compound according to Formula 2

Formula 2

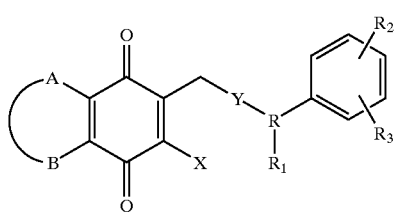

where A and B are independently selected from the group consisting of hydrogen and halogen, X is either a hydrogen or halogen atom, Y is a single bond, R is nitrogen, $R_1$ is hydrogen, $R_2$ is para to R and is selected from the group consisting of adamantyl ester, —CH$_2$adamantyl ester, isopropyl ester, methyl ester and t-butyl ester, and $R_3$ is either ortho or meta respect to R, and is selected from the group consisting of hydrogen, hydroxyl and halogen; and a material selected from the group consisting of inert carriers, excipients, diagnostics, direct compression binders, buffers, solvents, stabilizers, fillers, disintegrants, flavors, colors, lubricants, other active ingredients, other materials conventionally used in the formulation of pharmaceutical compositions, and mixtures thereof.

12. A pharmaceutical composition, comprising:

an amount of a compound effective to inhibit the proliferation of cells in a subject, the compound having an in vivo biological activity of 4 or greater as measured by an IP+SC score, the compound satisfying Formula 1

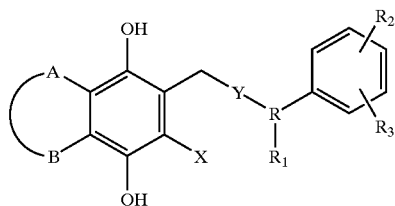

Formula 1 where A and B independently are selected from the group consisting of hydrogen and halogen, or are carbon atoms in an aromatic ring, X is either hydrogen or halogen, Y is either a single bond or a double bond, R is carbon or nitrogen, $R_1$ is hydrogen or an aliphatic group, $R_2$, is either meta or para to R and is selected from the group consisting of amino, aliphatic amine, aliphatic alcohols, aliphatic amides, aliphatic phosphonic acid esters, the aliphatic groups comprising from 1 to about 30 carbon atoms, aliphatic esters having from 3 to about 30 carbon atoms and aliphatic ketones having from 3 to about 30 carbon atoms, and $R_3$ is either ortho, meta or para to R and is selected from the group consisting of hydrogen, hydroxyl and halogen, or Formula 2

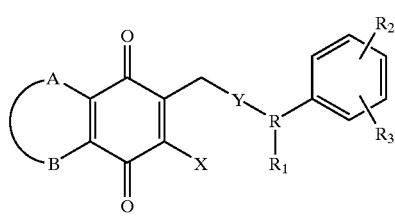

Formula 2 where A and B independently are selected from the group consisting of hydrogen and halogen, or both are carbon atoms in an aromatic ring, X is a halogen atom, Y is either a single bond or a double bond, R is either carbon or nitrogen, $R_1$ is hydrogen or an aliphatic group having from about 1 to about 30 carbon atoms, $R_2$ is meta or para to R and is selected from the group consisting of amino, aliphatic amine, aliphatic alcohols, aliphatic amides, aliphatic esters, aliphatic ketones and phosphonic acid esters with the aliphatic groups comprising from about 1–30 carbon atoms, and $R_3$ is either ortho, meta or para to R and is selected from the group consisting of hydrogen, hydroxyl and halogen; wherein the compound is selected from the group consisting of 4'-adamantylbenzoate-1'-2,5-dihydroxybenzylamine, 4'-adamantylmethylbenzoate-1'-N-2,5-dihydroxybenzylamine, 5'-chloro-4'-isopropylbenzoate-1'-N-2,5-dihydroxybenzylamine, 4'-(trifluoromethylethanol)-1'-N-2,5-dihydroxybenzylamine, 4'-phenylphosphonate-1-'N-2,5-dihydroxylbenzylamine, 4'isopropylbenzoate-1'-N-5-bromo-2,5-dihydroxybenzylamine, 4'-chloro-5'-methylbenzoate-1'-N-3-bromo-2,5-dihydroxybenzylamine, 5'-hydroxy-4'-methylbenzoate-1'-N-5-bromo-2,5-dihydroxybenzylamine, 3'-hydroxy-4'-methylbenzoate-1'-N-p-quinone-2-methyl amine, 4'-isopropylbenzoate-1'-N-p-quinone-2-methyl amine, 4'-adamantylbenzoate-1'-N-p-quinone-2-methyl amine, 4'-adamantylbenzoate-1'-N-2-bromo-p-quinone-3-methyl amine, 4'-t-butylbenzoate-1'-N-2-bromo-p-quinone-3-methyl amine, 3'-chloro-4'-methylbenzoate-1'-N-2-bromo-p-quinone-3-methyl amine, 3'-chloro-4'-isopropylbenzoate-1'-N-p-quinone-2-methyl amine and mixtures thereof; and a material selected from the group consisting of inert carriers, excipients, diagnostics, direct compression binders, buffers, solvents, stabilizers, fillers, disintegrants, flavors, colors, lubricants, other active ingredients, other materials conventionally used in the formulation of pharmaceutical compositions, and mixtures thereof.

13. A pharmaceutical composition for inhibiting the proliferation of living cells, comprising:

an effective amount of a compound having structural Formula 1 and/or 2;

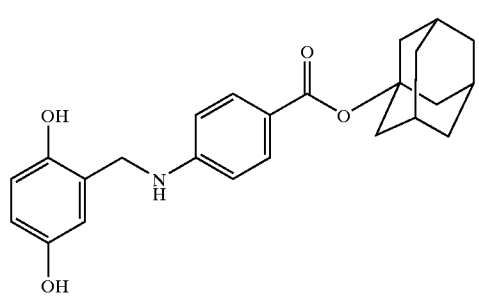

Formula 1

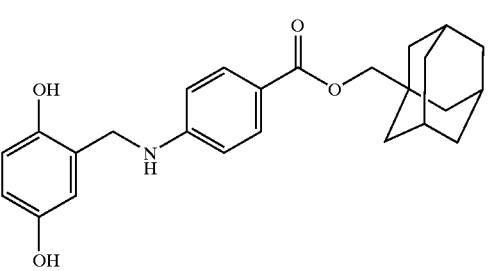

Formula 2 and a material selected from the group consisting of inert carriers, excipients, diagnostics, direct compression binders, buffers, solvents, stabilizers, fillers, disintegrants, flavors, colors, lubricants, other active ingredients, other materials conventionally used in the formulation of pharmaceutical compositions, and mixtures thereof.

14. A method for inhibiting the proliferation of living cells in a subject, comprising:

providing a compound, or a composition comprising the compound, having an in vivo biological activity of 4 or greater as measured by an IP+SC score, the compound satisfying Formula 1

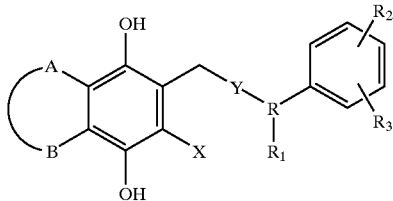

Formula 1 where A and B independently are selected from the group consisting of hydrogen and halogen, or are carbon atoms in an aromatic ring, X is either hydrogen or halogen, Y is a single bond or a double bond, R is carbon or nitrogen, $R_1$ is hydrogen or an aliphatic group, $R_2$ is either meta or para to R and is selected from the group consisting of amino, aliphatic amines, aliphatic alcohols, aliphatic amides, aliphatic ketones aliphatic phosphonic acid esters, the aliphatic groups comprising from 1 to about 30 carbon atoms, and aliphatic esters having from 3 to about 30 carbon atoms, and $R_3$ is either ortho, meta or para to R and is selected from the group consisting of hydrogen, hydroxyl and halogen, or Formula 2

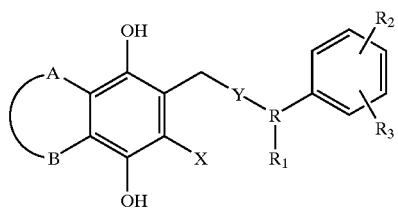

Formula 2 where A and B independently are selected from the group consisting of hydrogen and halogen, or both are carbon atoms in an aromatic ring, X is a halogen atom, Y is either a single bond or a double bond, R is either carbon or nitrogen, $R_1$ is hydrogen or an aliphatic group having from about 1 to about 30 carbon atoms, $R_2$ is meta or para to R and is selected from the group consisting of amino, aliphatic amine, aliphatic alcohols, aliphatic amides, aliphatic esters, aliphatic ketones and phosphonic acid esters, with the aliphatic groups comprising from about 1–30 carbon atoms, and $R_1$ is either ortho, meta or para to R and is selected from the group consisting of hydrogen, hydroxyl and halogen; and administering an effective amount of the compound, or composition comprising the compound, to the subject to inhibit the proliferation of living cells in the subject.

15. The method according to claim 14 where the compound satisfies Formula 1 and where A and B are independently selected from the group consisting of hydrogen and halogen, X is either hydrogen or halogen, Y is a single bond, R is nitrogen, $R_1$ is hydrogen, $R_2$ is para to R and is selected from the group consisting of adamantyl ester, —CH$_2$adamantyl ester, isopropyl ester, t-butyl ester, diisopropyl amide, trifluromethylisopropyl alcohol and aliphatic phosphonic acid ester and $R_3$ is either ortho or meta to R and is selected from the group consisting of hydrogen, hydroxyl and halogen, or Formula 2 where A and B are independently selected from the group consisting of hydrogen and halogen, X is either a hydrogen or halogen atom, Y is a single bond, R is nitrogen, $R_1$ is hydrogen, $R_2$ is para to R and is selected from the group consisting of adamantyl ester, —CH$_2$adamantyl ester, isopropyl ester, methyl ester and t-butyl ester, and $R_3$ is either ortho or meta R and is selected from the group consisting of hydrogen, hydroxyl and halogen.

16. The method according to claim 14 where administering comprises administering the compound or composition topically, orally, intramuscularly, intranasally, subcutaneously, intraperitoneally, intralesionally or intravenously.

17. The method according to claim 14 where the effective amount comprises from about 0.1 gram to about 3.0 grams of the compound.

18. The method according to claim 14 where the effective amount comprises from about 30 mg/kg of subject/dose to about 50 mg/kg of subject/dose.

19. The method according to claim 14 wherein the compound has the structural formula

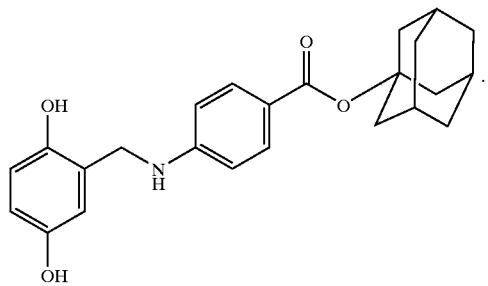

20. A method for inhibiting the proliferation of living cells in a subject, comprising:

providing a compound, or a composition comprising the compound, having Formula 1

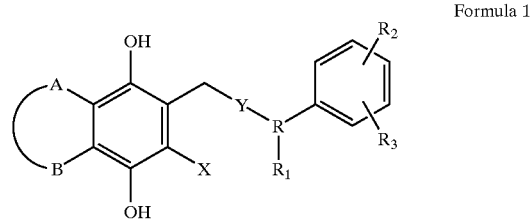

Formula 1 where A and B independently are selected from the group consisting of hydrogen and halogen, X is either hydrogen or halogen, Y is a single bond, R is nitrogen, $R_1$ is hydrogen, $R_2$ is para to R and is selected from the group consisting of adamantyl ester, —CH$_2$adamantyl ester, isopropyl ester, t-butyl ester, diisopropyl amide, trifluoromethylisopropyl alcohol, and aliphatic phosphonic acid ester and $R_3$ is either ortho or meta to R and is selected from the group consisting of hydrogen, hydroxyl and halogen, or Formula 2

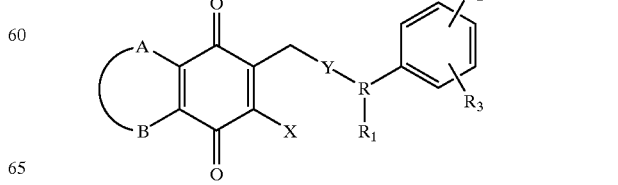

Formula 2 where A and B independently are selected from the group consisting of hydrogen and halogen, X is hydrogen or halogen, Y is a single bond, R is nitrogen, $R_1$ is hydrogen, $R_2$ is para to R and is selected from the group consisting of adamantyl ester, —$CH_2$adamantyl ester, isopropyl ester, methyl ester, t-butyl ester, and $R_3$ is either ortho, meta or para with R, and is selected from the group consisting of hydrogen, hydroxyl and halogen, and administering from about 0.1 grams to about 3.0 grams of the compound, or a composition comprising the compound, topically, orally, intramuscularly, intranasally, subcutaneously, intraperitoneally, intralesionally or intravenously to the subject to inhibit the proliferation of living cells in the subject.

21. The method according to claim 20 wherein the compound has the structural formula

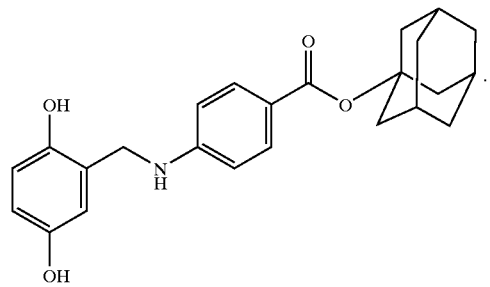

22. The method according to claim 17 where from about 30 mg/kg of subject/dose of the compound is administered to the subject.

* * * * *